(12) United States Patent
Sudam et al.

(10) Patent No.: US 9,974,944 B2
(45) Date of Patent: May 22, 2018

(54) SUBCUTANEOUS LEADS AND METHODS OF IMPLANT AND EXPLANT

(75) Inventors: Abdulkader Sudam, Laguna Niguel, CA (US); Tim Fonte, San Francisco, CA (US); Todd Kerkow, San Clemente, CA (US); Alan Marcovecchio, San Clemente, CA (US)

(73) Assignee: Cameron Health, Inc., St. Paul ( * ) Notice: Subject to any disclaimer, the term of this patent is extended or adjusted under 35 U.S.C. 154(b) by 1835 days.

(21) Appl. No.: 13/194,632

(22) Filed: Jul. 29, 2011

(65) Prior Publication Data

US 2012/0029335 A1 Feb. 2, 2012

Related U.S. Application Data

(60) Provisional application No. 61/368,937, filed on Jul. 29, 2010.

(51) Int. Cl.
*A61N 1/05* (2006.01)

(52) U.S. Cl.
CPC .............. *A61N 1/05* (2013.01); *A61N 1/0504* (2013.01)

(58) Field of Classification Search
CPC .............................. A61N 1/05; A61N 1/0587
USPC ............. 607/122, 130, 126, 5, 119; 606/129
See application file for complete search history.

(56) References Cited

U.S. PATENT DOCUMENTS

| | | | |
|---|---|---|---|
| 3,902,501 A * | 9/1975 | Citron et al. | 607/126 |
| 4,437,475 A * | 3/1984 | White | 607/126 |
| 5,105,826 A | 4/1992 | Smits et al. | |
| 5,746,722 A | 5/1998 | Pohndorf et al. | |
| 5,755,767 A | 5/1998 | Doan et al. | |
| 5,902,329 A | 5/1999 | Hoffmann et al. | |
| 6,136,021 A | 10/2000 | Tockman et al. | |
| 6,256,542 B1 | 7/2001 | Marshall | |
| 6,501,993 B2 | 12/2002 | Morgan et al. | |
| 6,647,292 B1 | 11/2003 | Bardy et al. | |
| 6,712,826 B2 | 3/2004 | Lui | |
| 6,721,597 B1 | 4/2004 | Bardy et al. | |
| 6,754,528 B2 | 6/2004 | Bardy et al. | |
| 6,934,589 B2 | 8/2005 | Sundquist et al. | |
| 7,090,682 B2 | 8/2006 | Sanders et al. | |
| 7,149,575 B2 | 12/2006 | Ostroff et al. | |
| 7,194,302 B2 | 3/2007 | Bardy et al. | |

(Continued)

OTHER PUBLICATIONS

Lang, Douglas J., et al; Implantable Cardioverter Defibrillator Lead Technology: Improved Performance and Lower Defibrillation Thresholds; PACE; vol. 18; pp. 548-559; Mar. 1995, Pt II.

(Continued)

*Primary Examiner* — Carl H Layno
*Assistant Examiner* — Jon Eric C Morales
(74) *Attorney, Agent, or Firm* — Seager, Tufte & Wickhem LLP

(57) ABSTRACT

New and/or alternative designs for implantable leads that have fixation structures to keep leads at a desired location after implant. Fixation structure may take several forms that create distally located fixation for use primarily in subcutaneous implantation. Some examples include new and/or alternative methods of implanting such leads. Some examples also include fixation structures, such as a suture sleeve, that can be attached to a lead for fixation thereof. Some further examples show methods of implanting a subcutaneous lead, and others include methods of extracting implanted subcutaneous leads.

16 Claims, 23 Drawing Sheets

(56) References Cited

U.S. PATENT DOCUMENTS

| | | | |
|---|---|---|---|
| 7,218,970 B2 | 5/2007 | Ley et al. | |
| 7,218,971 B2 | 5/2007 | Heil, Jr. et al. | |
| 7,236,829 B1 | 6/2007 | Farazi et al. | |
| 7,248,921 B2 | 7/2007 | Palreddy et al. | |
| 7,376,458 B2 | 5/2008 | Palreddy et al. | |
| 7,392,085 B2 | 6/2008 | Warren et al. | |
| 7,463,933 B2 | 12/2008 | Wahlstrom et al. | |
| 7,477,935 B2 | 1/2009 | Palreddy et al. | |
| 7,499,758 B2 | 3/2009 | Cates et al. | |
| 7,623,909 B2 | 11/2009 | Sanghera et al. | |
| 7,623,913 B2 | 11/2009 | Phillips | |
| 7,655,014 B2 | 2/2010 | Ko et al. | |
| 7,890,191 B2 | 2/2011 | Rutten et al. | |
| 8,437,867 B2 | 5/2013 | Murney et al. | |
| 2002/0049485 A1* | 4/2002 | Smits | 607/122 |
| 2003/0074041 A1* | 4/2003 | Parry et al. | 607/130 |
| 2004/0102804 A1* | 5/2004 | Chin | 606/190 |
| 2004/0230274 A1 | 11/2004 | Heil et al. | |
| 2006/0167503 A1 | 7/2006 | Warren et al. | |
| 2006/0247753 A1 | 11/2006 | Wenger et al. | |
| 2008/0046056 A1* | 2/2008 | O'Connor | A61N 1/05 607/119 |
| 2008/0196939 A1 | 8/2008 | Lubenow et al. | |
| 2009/0036944 A1 | 2/2009 | Fonte | |
| 2009/0187227 A1 | 7/2009 | Palreddy et al. | |
| 2009/0198295 A1 | 8/2009 | Dennis et al. | |
| 2009/0198296 A1 | 8/2009 | Sanghera et al. | |
| 2009/0228057 A1 | 9/2009 | Allavatam et al. | |
| 2009/0248054 A1 | 10/2009 | Sage et al. | |
| 2009/0276025 A1 | 11/2009 | Burnes et al. | |
| 2009/0312712 A1 | 12/2009 | Olson | |
| 2010/0030311 A1 | 2/2010 | Lazeroms et al. | |
| 2010/0152798 A1 | 6/2010 | Sanghera et al. | |
| 2011/0082516 A1 | 4/2011 | Kast et al. | |
| 2011/0245645 A1 | 10/2011 | Kenngott et al. | |

OTHER PUBLICATIONS

Haqqani, Hans M., et al.; Review—The Implantable Cardioverter-Defibrillator Lead: Principles, Progress, and Promises; PACE; vol. 32; pp. 1336-1353; Oct. 2009.
U.S. Appl. No. 61/255,253; filed Oct. 27, 2009; Allavatam, et al.
U.S. Appl. No. 61/255,249; filed Oct. 27, 2009; Warren, et al.
U.S. Appl. No. 61/221,316; filed Jun. 29, 2009; Allavatam, et al.

* cited by examiner

Wrap "wings" around beneath distal electrode

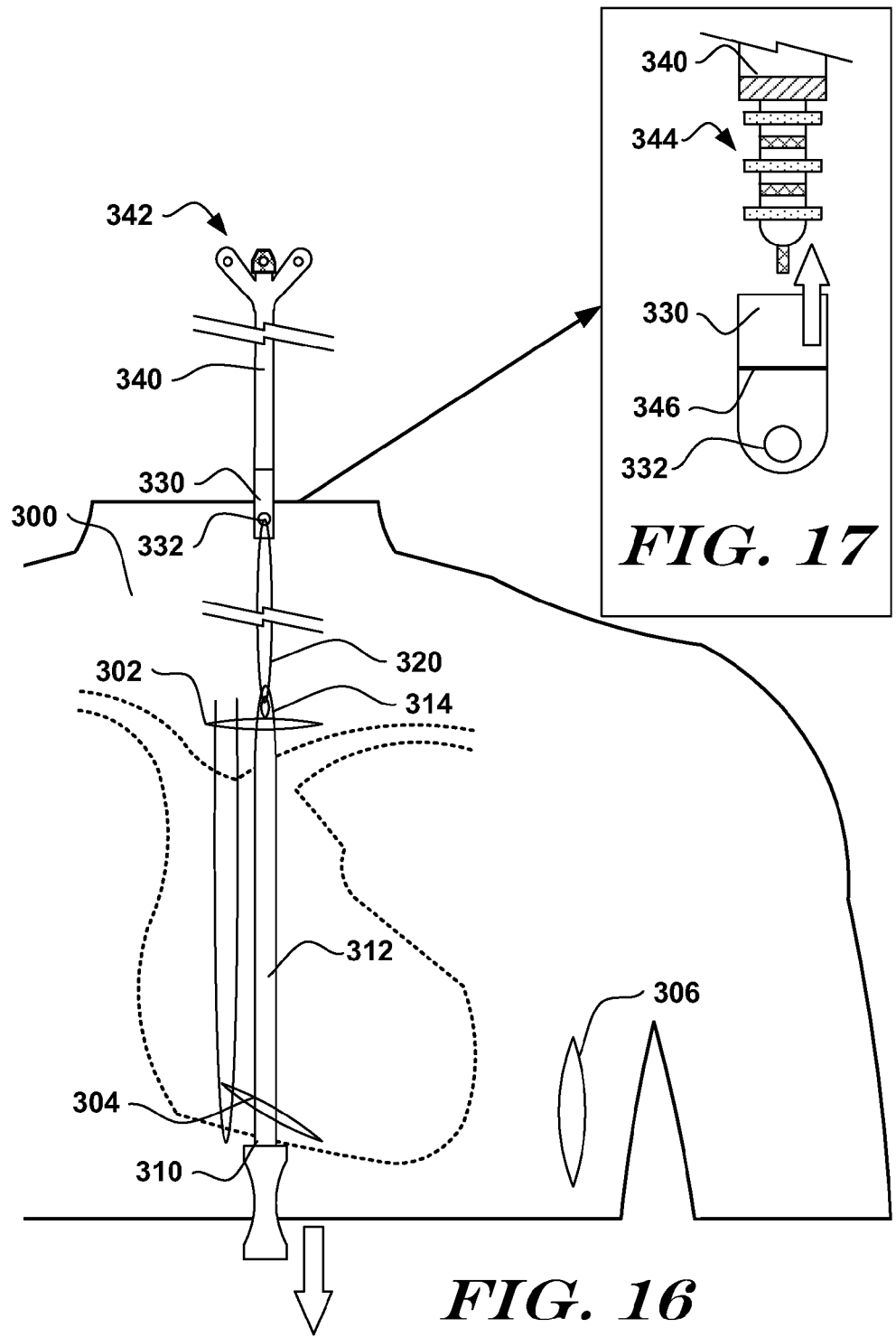

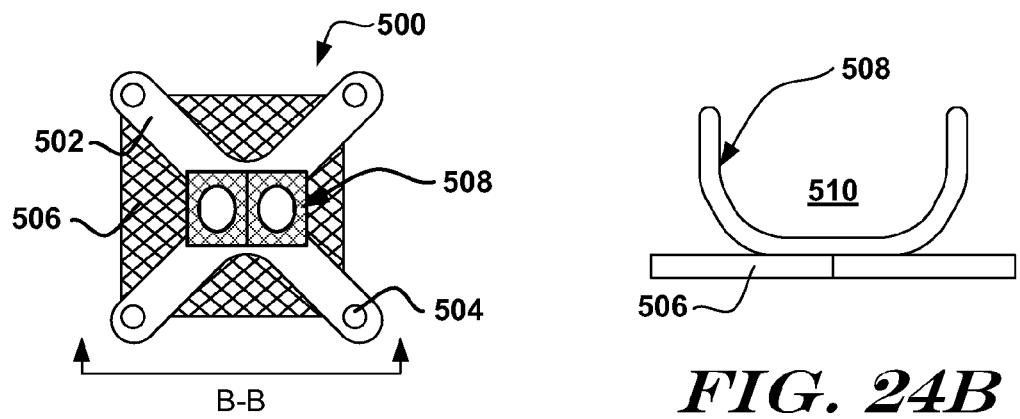
*FIG. 24A*
*FIG. 24B*
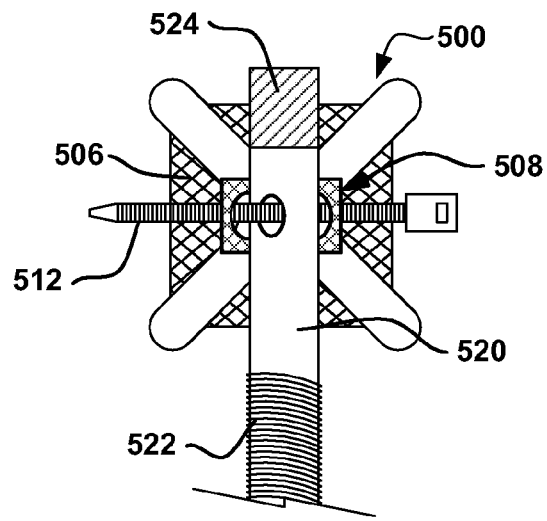
*FIG. 24C*

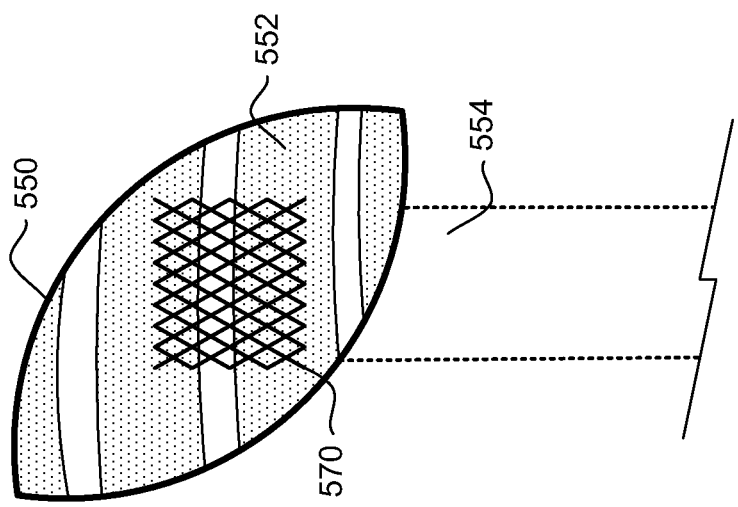
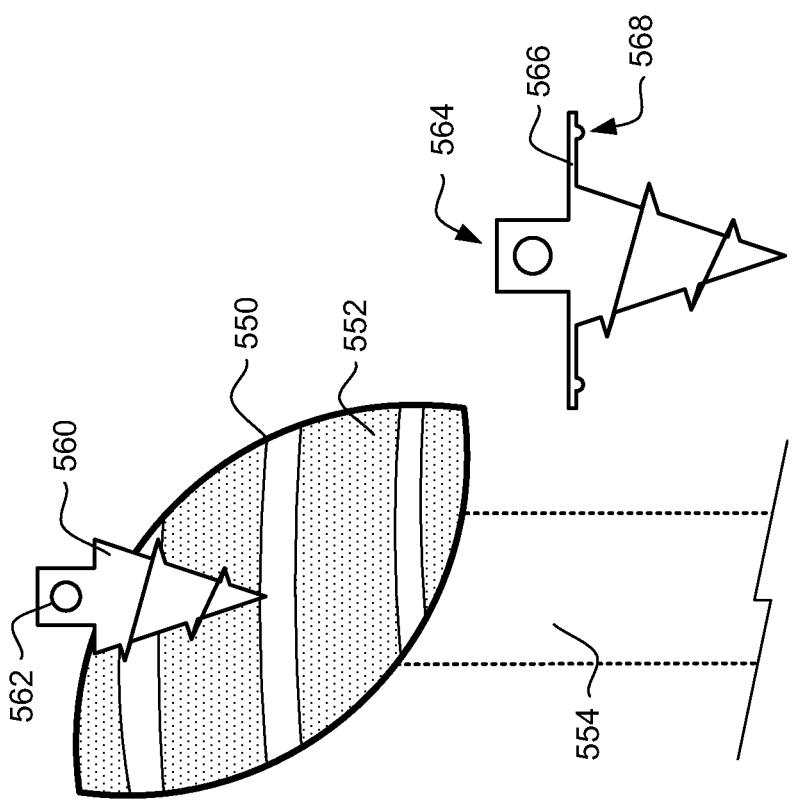
FIG. 24E
FIG. 24D

SUBCUTANEOUS LEADS AND METHODS OF IMPLANT AND EXPLANT

RELATED APPLICATIONS

The present application claims the benefit of and priority to U.S. Provisional Application 61/368,937, titled SUBCUTANEOUS LEADS AND METHODS OF IMPLANT AND EXPLANT, the disclosure of which is incorporated herein by reference.

FIELD

The present invention relates to the field of implantable medical devices. More particularly, the present invention relates to the field of implantable stimulus devices having subcutaneous leads.

BACKGROUND

Implantable defibrillators have become an accepted therapy for individuals living with a likelihood of sudden cardiac arrest. Early systems used epicardial electrodes attached to the exterior of the heart. However, epicardial placement of leads/electrodes presented numerous challenges such as the invasive procedure and long-term problems from electrode attachment to the exterior of the heart. Later systems moved to the use of transvenous leads which did not require thoracotomy for lead placement. Transvenous systems, however, are susceptible to difficulties in electrode placement and lead durability, compounded by the fact that failed leads may require difficult removal from within the heart and veins. Subcutaneous-only systems represent an option to avoid transvenous leads. New and/or alternative methods for subcutaneous lead placement, new and/or alternative lead designs, and new and/or alternative methods and systems for subcutaneous lead fixation are desired.

SUMMARY

Several embodiments include new and/or alternative designs for subcutaneously implantable leads. Some embodiments include leads for subcutaneous implantation using fixation structures. Some embodiments include new and/or alternative methods of implanting such leads. Some embodiments also include fixation structures that can be attached to a lead for fixation thereof. Some further embodiments include methods of extracting implanted subcutaneous leads and designs for such leads configured to new and/or alternative extraction methods.

BRIEF DESCRIPTION OF THE DRAWINGS

FIGS. 16-21 show another illustrative method of implanting a subcutaneous cardiac device;

FIGS. 24A-24E demonstrate a reusable subcutaneous anchoring structure;

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives. In the methods shown below, structures may be beneath the skin and over the ribcage of the patient, though such elements are not always shown in phantom. Reference to incisions that are entry and exit points for these structures are provided for clarity.

The words "proximal" and "distal" are used herein to differentiate the end of a lead that couples to the canister of an implantable system (the proximal end) from the end of the lead that is not attached to the canister of an implantable system (the distal end). No specific anatomical significance is intended. For example, the distal end of a lead is not necessarily anatomically distal relative to the proximal end of the lead; anatomic distal and proximal terminology will be determined by the final implantation location(s).

Figure 1:
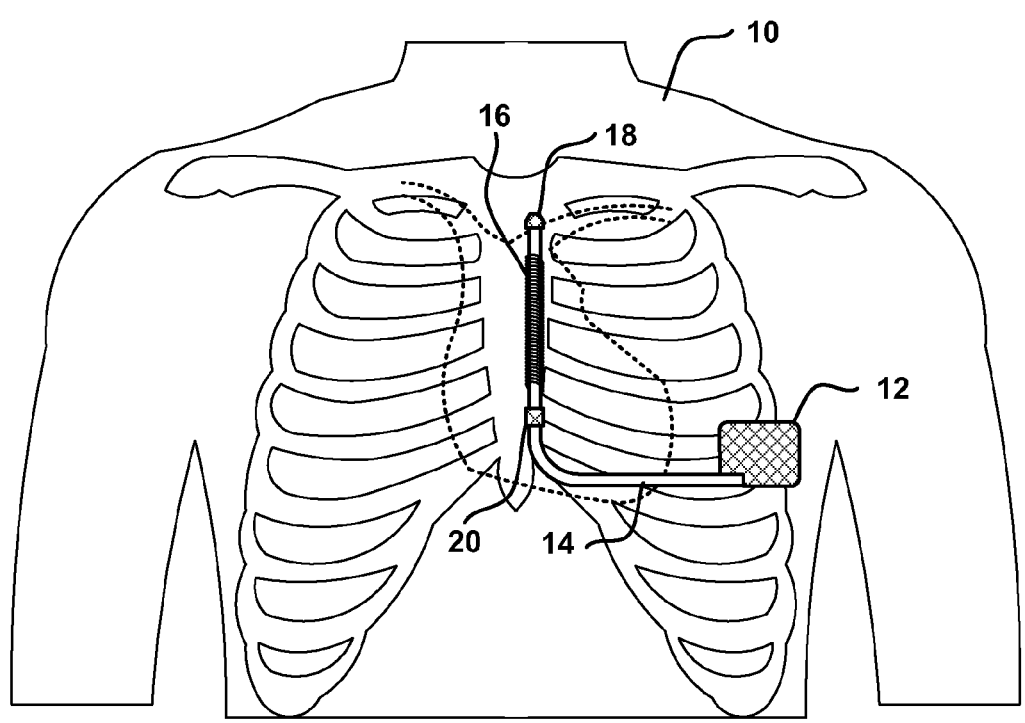
FIG. 1 shows an illustrative placement for an implantable subcutaneous defibrillator.

FIG. 1 shows an illustrative placement for an implantable subcutaneous defibrillator. The system is shown implanted in a patient 10, for whom certain anatomical features are outlined including the ribcage and heart. The subcutaneous defibrillator includes a canister 12 implanted near the left axilla, about level with the inframammary crease, with a lead 14 extended medially toward the sternum and xiphoid of the patient 10. Near but just to the left of the sternum, the lead 14 is directed superiorly along the sternum. The lead 14 is shown having three electrodes including a coil electrode 16 and two smaller electrodes 18, 20 disposed along the left margin of the sternum. More or fewer electrodes may be provided and various functions can be performed using each electrode 16, 18, 20. Some examples of leads and electrode spacing are shown in U.S. Patent Application Publication Number US 2010-0152798 A1, titled ELECTRODE SPACING IN A SUBCUTANEOUS IMPLANTABLE CARDIAC STIMULUS DEVICE, the disclosure of which is incorporated herein by reference, though other structural and spacing configurations may be used as well.

The lead 14 carries electrical conductors that allow electrical coupling of electronics in the canister 12 to the electrodes 16, 18, 20. In some examples the lead 14 is extruded with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends can be used. In some embodiments, a conductor for one of electrodes 16, 18, 20 may serve as a strengthening member onto which the body of the lead 14 is extruded. For example, the distal electrode 18 may couple to a centrally located wire on which the body of lead 14 is extruded. Conductors in the lead 14 may take the form of wires of any suitable conductive material and construction, such as stainless steel (for example, MP35N steel), silver, copper or other conductive materials, which may have separate coatings or sheathing for anticorrosive, insulative and/or protective reasons. The conductors may take various forms including wires, drawn filled tubes and/or helical coiled conductors, for example.

The implant location shown in FIG. 1 is merely illustrative of one of several locations that can be used for implantation of a subcutaneous defibrillator system. While this location is shown repeatedly in the later figures, it should be understood that other locations such as shown in U.S. Pat. Nos. 6,647,292, 6,721,597, 7,194,302, 7,149,575 and/or 7,655,014, which are incorporated herein by reference, may be used as well. For example, in some embodiments, the canister 12 may be located at a higher, upper pectoral location closer to the clavicle, or it may be located in a more anterior/medial location nearer to the sternum. In other embodiments, the canister 12 may be located more posteriorly or even abdominally or, in certain examples, on the right side of the patient. The lead 14 may extend across to the right side of the patient or it may extend around the patient's chest to a posterior location in other examples. Multiple leads can be used. If desired, in addition to a subcutaneous lead, an endocardial lead (such as a transvenous lead) or epicardial lead may also be placed.

Figure 2:
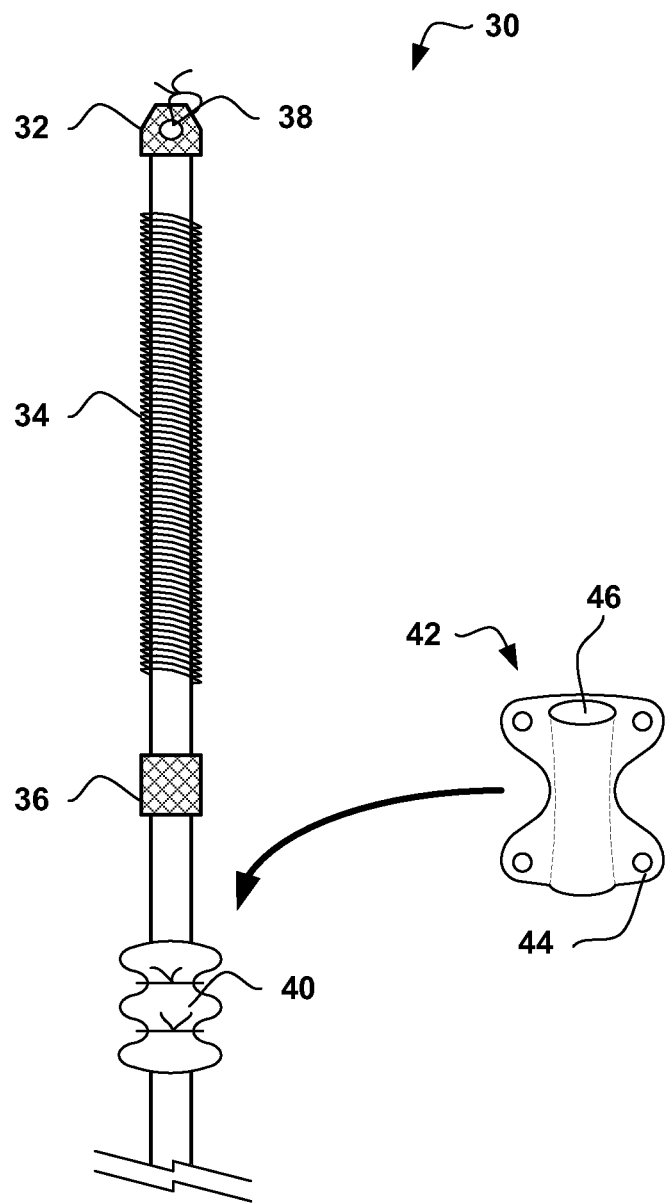
FIG. 2 shows an illustrative distal portion of a subcutaneous lead from FIG. 1 having fixation sutures placed thereon.

FIG. 2 shows an illustrative distal portion of a subcutaneous lead from FIG. 1 having fixation sutures placed thereon. The subcutaneous lead 30 is shown including a distal tip electrode 32, a coil electrode 34 and a proximal electrode 36. An attachment feature is shown at the distal tip electrode 32 as a suture hole 38. A suture sleeve is shown at 40 as well. The suture hole 38 and suture sleeve 40 can be used to suture the lead into position in the subcutaneous tissue of a patient, providing anchoring of the lead 30.

An alternative to suture sleeve 40 is shown at 42, with a suture sleeve 42 having a bore 46 for passing a lead 30 there through. Several attachment openings are provided on a plurality of leaflets that come off of the main body of the suture sleeve 40, as shown at 44. Sutures may be wrapped about the suture sleeve 42 and bore 46 and/or sutures may be applied on the attachment openings 44. Rather than attachment openings, a thin, pierce-able material or mesh can be used for the leaflets. A slit or gap can be provided to pass the lead 30 through the wall of the suture sleeve 42 into bore 46.

Figure 3A:
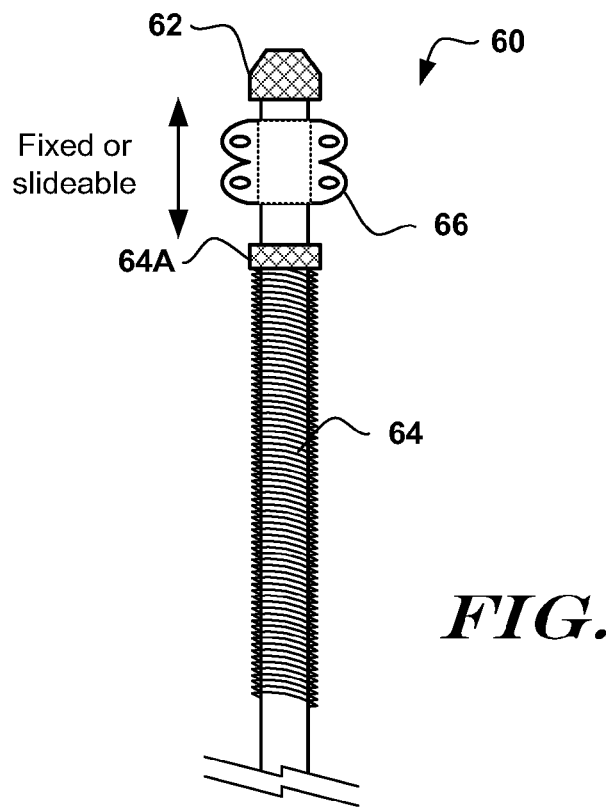
FIG. 3A illustrates an embodiment of a lead with a fixation apparatus located between two distal electrodes thereof.

FIG. 3A illustrates an embodiment of a lead with a moveable fixation apparatus located between two distal electrodes thereof. The lead 60 is shown with a distal electrode at 62 and a more proximal electrode shown at 64. As shown at 64A, the proximal electrode 64 may optionally include a distal "stopper" 64A, shown as a thickened ring for the example. The stopper 64A may be part of the electrode 64 and may be conductive or, alternatively, the stopper 64A can be a non-conductive element. A suture sleeve 66 is shown disposed between the distal electrode 62 and the stopper 64A. The suture sleeve 66 may be fixed or slidable on the lead 60 between the stopper 64A and the distal electrode 62.

In some examples, the stopper 64A may be omitted. For example, the suture sleeve 66 may be affixed to lead 60 before implant, or the suture sleeve 66 can be attached onto the lead 60 by tightening a suture thereover. In another example electrode 64 may be of sufficient diameter to block passage of a slidable suture sleeve 66, allowing the stopper 64A to be omitted. In another example, the suture sleeve may slide over the lead 60 until it reaches the distal electrode 62 and the lead can be prevented from migrating back toward the canister by placement of the suture sleeve 66. In such a configuration, forces following implant may urge the lead to migrate back toward the canister but not to advance in the other direction, such that stopping movement in one direction is sufficient. In other examples, it may be advisable to have the stopper 64A to ensure that the lead cannot move toward the spine, for a posteriorly located lead, or toward the neck for a system as shown in FIG. 1. For some implant locations, maintaining specific positions for one or more electrodes for sensing or stimulus purposes may create or imply a need for arresting movement in any direction. Whether any of these considerations apply may vary depending on patient, location or system specific characteristics.

In some examples, the area proximal of the stopper 64A is referred to as a suture sleeve receiving area. In some examples, the area between the distal electrode 62 and electrode 64 is referred to as the suture sleeve receiving area. In some examples, the lead 60 includes several lumens along a proximal portion of its length to carry wires (of any suitable form) coupling electrode 64 to the proximal end of the lead 60 (and hence to an attached pulse generator or monitoring housing), while the area distal of electrode 64 is of reduced diameter to receive the suture sleeve. For example, two separate pieces of tubing may be used, or a single multi-lumen element may be cut, compressed or ground to a reduced diameter distal of electrode 64. In one example, a wire is used to provide longitudinal reinforcement along the entire length of the lead 60 and to electrically connect the distal electrode 64 to the proximal end of the lead by coextrusion, either as a centrally located wire or offset to one side, for example.

Figure 3B:
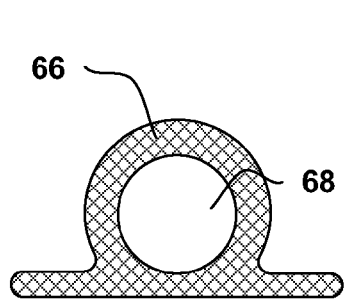
FIGS. 3B-3C show characteristics of the fixation apparatus from FIG. 3A.
Figure 3C:
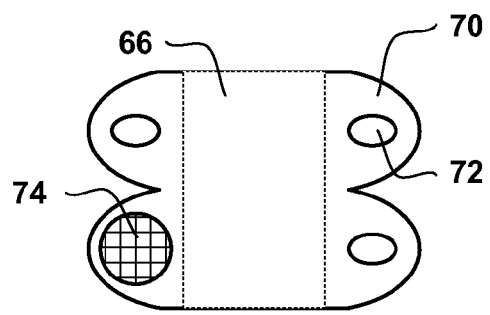

FIGS. 3B-3C show characteristics of the fixation apparatus from FIG. 3A. The suture sleeve 66 is shown in FIG. 3B as including a bore 68, which is sized to receive at least a portion of the lead. In some examples, the suture sleeve may be pre-loaded on the lead by the use of a heat-shrink process to reduce the bore 68 to an appropriate inner diameter for sliding disposition on the lead. In other example, the body forming the bore 68 of the suture sleeve 66 may be flexible to allow it to stretch and pass over the electrode 62 during implant.

In another example, the body of the suture sleeve 66 may be formed of a swellable material such that it can be placed on the lead before implantation and, once wetted at implant, the illustrative suture sleeve swells to prevent removal from the lead. In yet another example, the body of the suture sleeve 66 may include a gap or slit (not shown) for placement transversely onto the lead. In another example, the body of the suture sleeve is flexible enough to allow a suture to be tightened thereon to secure it to the lead.

In some embodiments, it is desirable to have the suture sleeve 66 moveable relative to the rest of the lead 60 in order to create some "play" or strain relief in the placement of the system. In other embodiments the suture sleeve 66 is fixed onto the lead by heat shrinking, adhesive or structural attachment, for example. In some embodiments, tying the suture around the suture sleeve 66 while it is on the lead 60 can tighten the suture sleeve 66 so it does not slide along the lead 60.

FIG. 3C highlights parts of the structure of the suture sleeve. A number of leaflets 70 are provided on the suture sleeve 66. Some leaflets 70 are shown as including suture holes 72. Other leaflets 70 include sections of resilient material 74, which may include, for example, a Dacron or other tough material in the form of a thin sheet or mesh. The resilient material 74 is designed to allow secure attachment to a suture without a defined opening or hole. A resilient material 74 may be used in place of any of the suture holes shown in any of the examples herein. The suture sleeve 66 may include each of these structures 72, 74 or may include only one of the two 72, 74. One may also use a surgical staple or screw to secure the suture sleeve 66 in place in the subcutaneous tissue of a patient. In another example, the leaflets 70 and/or the body of the suture sleeve 66 may be coated with a surgical adhesive which may be activated by coming into contact once wetted either due to tissue contact or by irrigation with saline or water during surgery or by irrigation with a liquid containing an activation chemical that interacts with the coating. The fixation structures (mesh, membrane or opening) and further features (including coatings) described for FIG. 3C may also be included as fixation features on any of the following embodiments.

Figure 4:
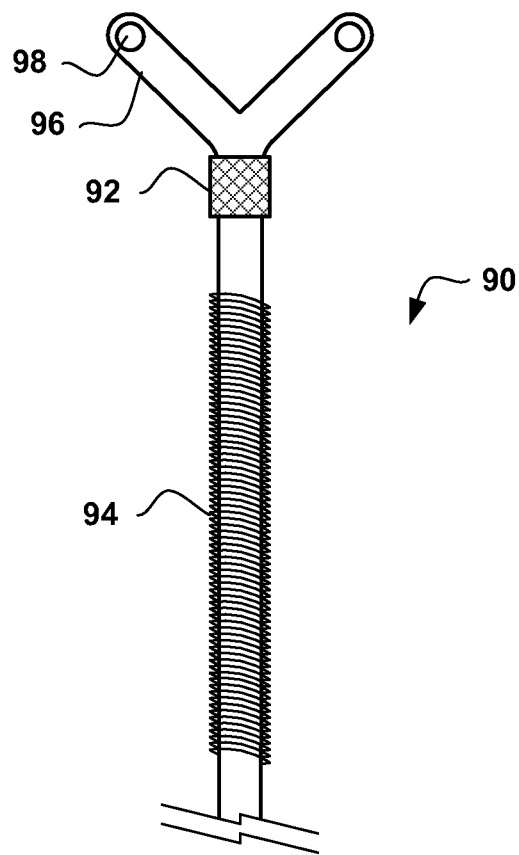
FIG. 4 illustrates a lead embodiment having a Y-shaped fixation structure at its distal end.

FIG. 4 illustrates a lead embodiment having a Y-shaped fixation structure at its distal end. The lead 90 is shown with a distal electrode 92 and a more proximal coil electrode 94. Distal of the distal electrode 92 is a Y-shaped structure having arms 96. The arms 96 may include a suture hole 98 or, as noted above, a suturing location taking the form of a mesh or sheet of tough material through which a suture or surgical staple can be placed. As can be seen, the arms 96 themselves provide a certain amount of anchoring since they are larger in dimension than the rest of the electrode and therefore are likely to be resistant to movement through the subcutaneous tunnel that the lead 90 passes through during implantation. For this reason, a special implant procedure as shown in FIGS. 16-21 may be used to implant lead 90 by pulling the proximal end thereof through tissue during implant, rather than passing the distal end of the lead 90 through a subcutaneous tunnel as shown by FIGS. 7-11. The arms 96 may be stiff or flexible in various embodiments. In one embodiment, arms 96 are generally flexible for implant but contain a material that becomes stiff due to irradiation, such as ultraviolet light (UV) curing, heating or after wetting or application of a curing substance, for example.

In another illustrative example, a lead electrode as shown in FIG. 4 may include relatively rigid arms 96. To implant this particular illustrative example, the user may dissect an area around an incision in which the Y-shaped structure is to be implanted, while also dissecting a subcutaneous tunnel through which the proximal end of the lead, but not the Y-shaped structure, can pass. The lead 90 would then be implanted by pulling its proximal end into the dissected tunnel, again as shown in FIGS. 16-21, below. The attachment features 98 on the arms 96 are optional for such an embodiment.

Figure 5A:
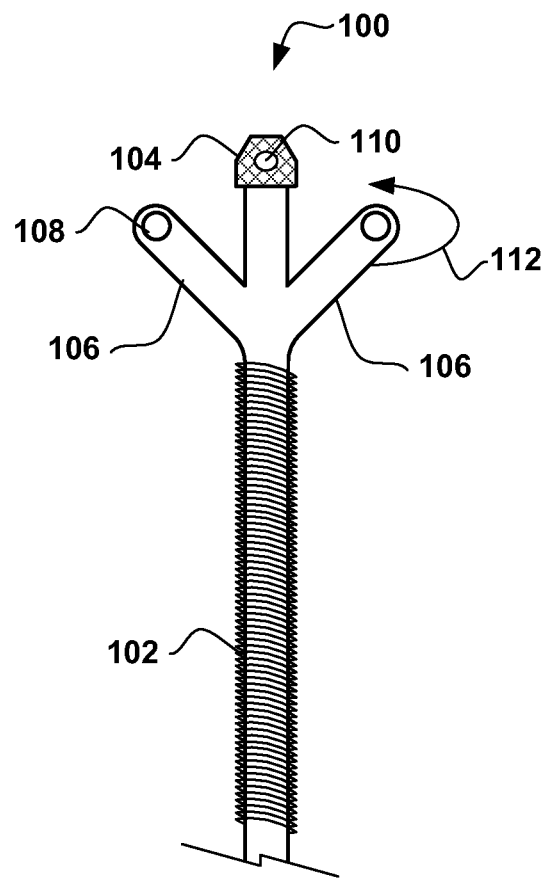
FIGS. 5A-5D illustrate lead embodiments having a distalmost electrode with "wings" that can be used for lead fixation.
Figure 5B:
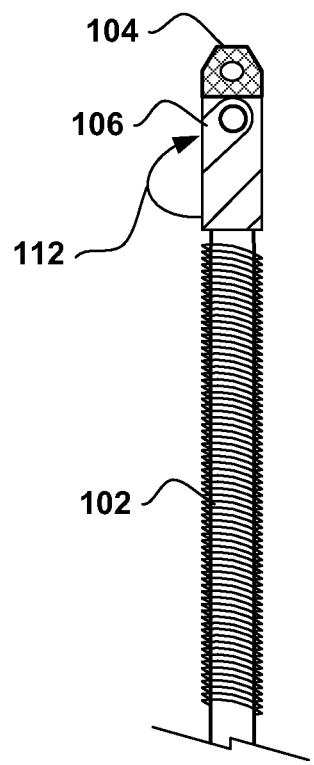

FIGS. 5A-5B illustrate lead embodiment having a distalmost electrode with "wings" that can be used for lead fixation. In this embodiment, the lead 100 includes a proximal electrode 102 and a distal tip electrode 104 (as with all other embodiments herein, additional electrodes may be included but are not shown). Between these two electrodes is an anchoring structure including two arms 106 having attachment locations shown as suture holes 108. Again, rather than suture holes 108, other anchoring structures such as a mesh or area of resilient material can be used instead. If desired, the distal tip electrode 104 may include an attachment feature such as the suture hole 110 that is shown.

The arms 106 may be flexible and can be wrapped around the lead 100, as shown by FIG. 5B. During implantation, the lead 100 may be implanted by pulling it through subcutaneous tissue from the proximal end, as shown in FIGS. 16-21, or by pulling from the distal end, as shown by FIGS. 7-11. If implanted by pulling from the distal end, the arms 106 maybe wrapped about the lead 100 as shown at 112 in FIG. 5B. A sheath may be provided over the distal portion of the lead 100 to keep the arms 106 in place or, alternatively, the arms may be kept in place during implantation by a dissolvable coating, such as an adhesive, stiction, or shaping such as thermoforming.

In one example, the arms 106 may also include a curable material that may be used to keep a desired Y-shape set after implantation, while allowing the arms to be flexible during implantation. Once set or cured, the arms 106 would be relatively inflexible and would reduce the likelihood of any migration of the lead. In order to explant, one may have to consider removing the lead by pulling from its distal end at the Y-shape, rather than the proximal end, as highlighted in FIG. 14, below. One may also cut and remove the Y-shape from the distal end of the lead 100. An alternative embodiment uses a T-shape rather than a Y-shape, which would have the arms extend at a right angle from the lead body.

Figures 5C, 5D:
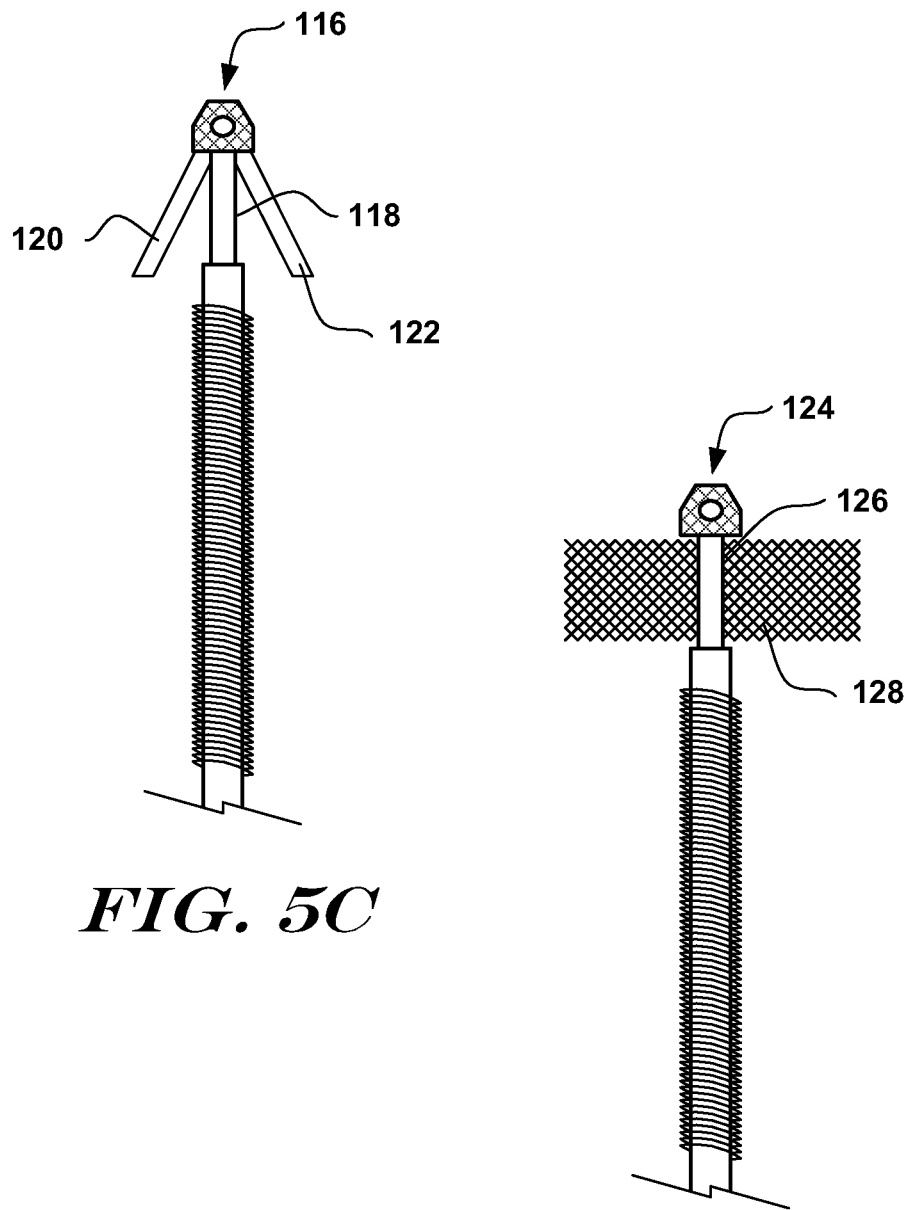

FIG. 5C shows another example similar to that of FIGS. 5A-5B except this time the flexible arms face toward the proximal end of the lead. The distal end of the lead 120 is shown, this time with a recessed portion 122 that can be used to receive arms 124, 126 during implantation (similar to FIG. 5B). In this example, the arms 124, 126 face away from the distal tip of the lead. During implantation, these arms 124, 126 can be wrapped as shown in FIG. 5B. It can be seen that this "proximal facing arm" configuration may be easier to use if the lead is implanted by pulling from its distal end, as the arms 124, 126 would smoothly pass through without being bent opposite of their final shape during implant, as would happen with the structure shown in FIG. 5A.

FIG. 5D shows another example, this time with a mesh material 128 attached to the lead near its distal tip 124 along a recessed region 126. Such a recess may be omitted in region 126, but is shown in this example. The mesh material 128 may use materials and structures as noted above for such a mesh. In place of a mesh material 128, a thin sheet that is ready for suturing to tissue can be used.

Figure 6A:
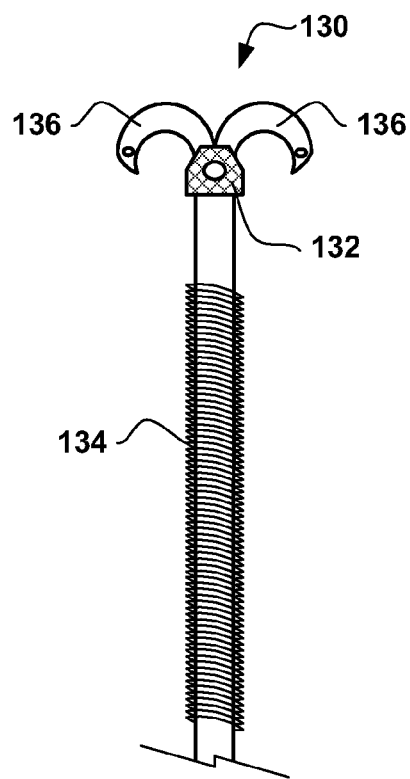
FIGS. 6A-6C illustrate lead embodiments having flexible arms at a distal portion.
Figure 6B:
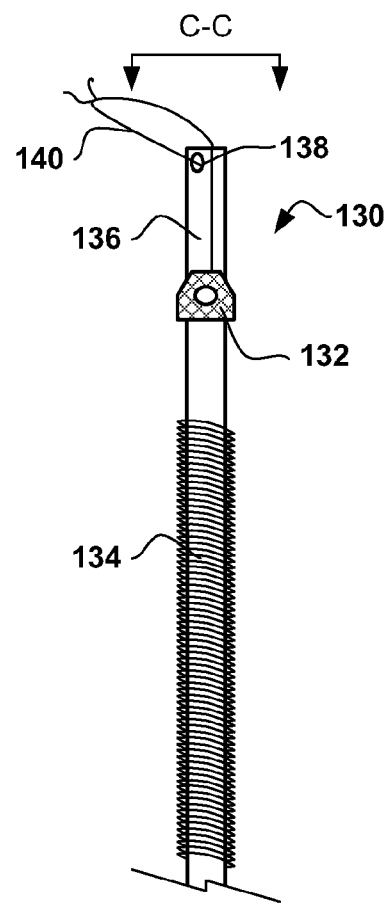
Figure 6C:
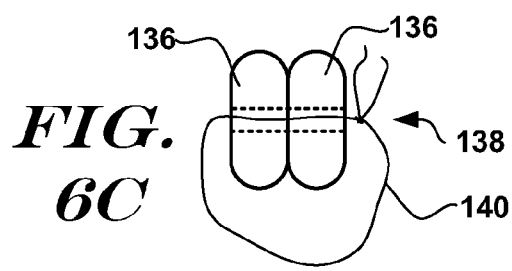

FIGS. 6A-6C illustrate a lead embodiment having flexible arms at a distal portion. Referring to FIG. 6A, the lead 130 includes a distal electrode 132 and two flexible arms 136 that extend distally from the distal electrode. A proximal electrode 134 is also shown. Other electrode configurations may be used instead.

Referring to FIG. 6B, the arms 136 are shown in an optional implant configuration extending generally in alignment with the rest of the lead 130 from the distal electrode, with the two arms 136 parallel to one another. In the embodiment shown, attachment features 138 in the form of suture holes are provided on the arms 136. In another embodiment, the attachment features 138 could instead be pieces or areas of resilient material adapted to receive a suture.

In the implanting configuration, the arms 136 are held together by the placement of a suture 140 through the attachment features 138. FIG. 6C highlights the side-by-side positioning of the arms 136 and alignment of the attachment features 138 in the implanting configuration. The side-by-side positioning creates a lower profile for implantation than appears in FIG. 6A. The suture 140 may be used as well to attach to an insertion tool. Thus the suture would serve to maintain the arms in a low profile implanting configuration while also coupling the distal tip of the lead 130 to an insertion tool. In a further example, the flexible arms 136 are secured together with a coating material that dissolves in response to contact with liquid during implantation, such as a biocompatible and soluble adhesive.

In another example, a removable cap can be provided over the distal arms 136 for use during implantation. In addition, other fixation structures can be used for attachment to the electrode insertion tool, such as a screw. Some examples of fixation between and electrode/lead and an implant tool are also shown in U.S. Patent Application Publication Number 2008-0046056, titled ELECTRODE INSERTION TOOLS, LEAD ASSEMBLIES, KITS AND METHODS FOR PLACEMENT OF CARDIAC DEVICE ELECTRODES, the disclosure of which is incorporated herein by reference.

FIGS. 7-11 show an illustrative method of implanting a subcutaneous defibrillator in a patient 150. Beginning with FIG. 7, certain anatomy of the patient 150 is highlighted including the heart 152 and sternum 154. A xiphoid incision 156 is made just to the left of and superior of the xiphoid near the lower portion of the sternum 154, and an axillary incision is made near the left axilla of the patient 150, as shown at 158.

An insertion tool 160 is used in the procedure. The insertion tool 160 has a handle 162 at its proximal end, and an elongate shaft 164 extends distally from the handle 162 toward a distal dissecting tip that includes an attachment feature 166. The attachment feature 166 is shown as a suture opening; other structures are noted below. The distal tip may be shaped for dissection of subcutaneous tissue. In one example, the distal tip has a tapered blunt tip, allowing for passage by dissection through subcutaneous tissue without encouraging piercing through the epidermis. A channel(s) may be provided in the insertion tool 160 to allow infusion of fluids for antiseptic, anti-inflammatory, pain reduction, or other purposes at the dissecting tip or along the length thereof. If ingrowth or adhesion is desired, a tissue adhesive or steroid may be infused as well.

Figure 7:
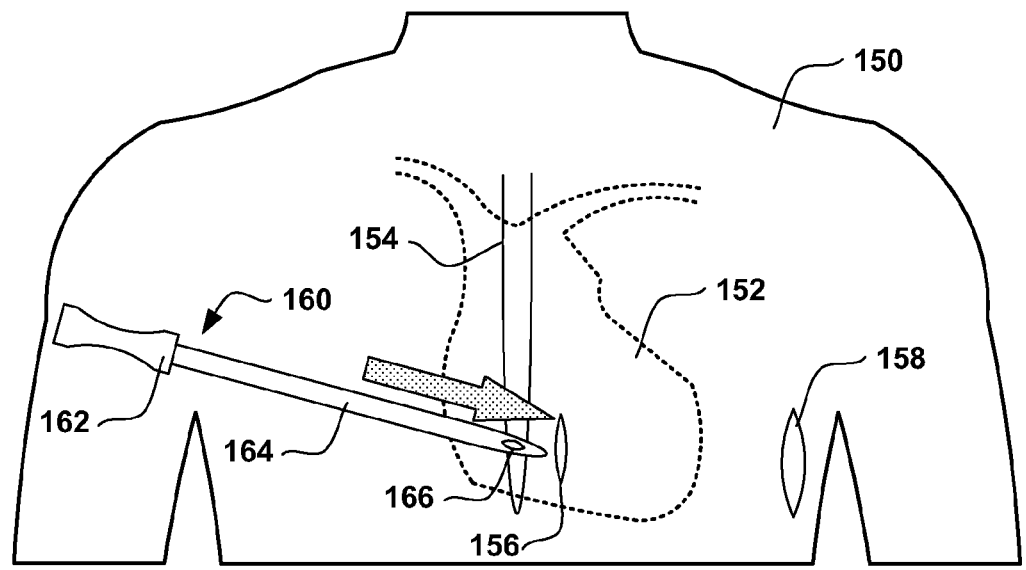
FIGS. 7-11 show an illustrative method of implanting a subcutaneous cardiac device.
Figure 8:
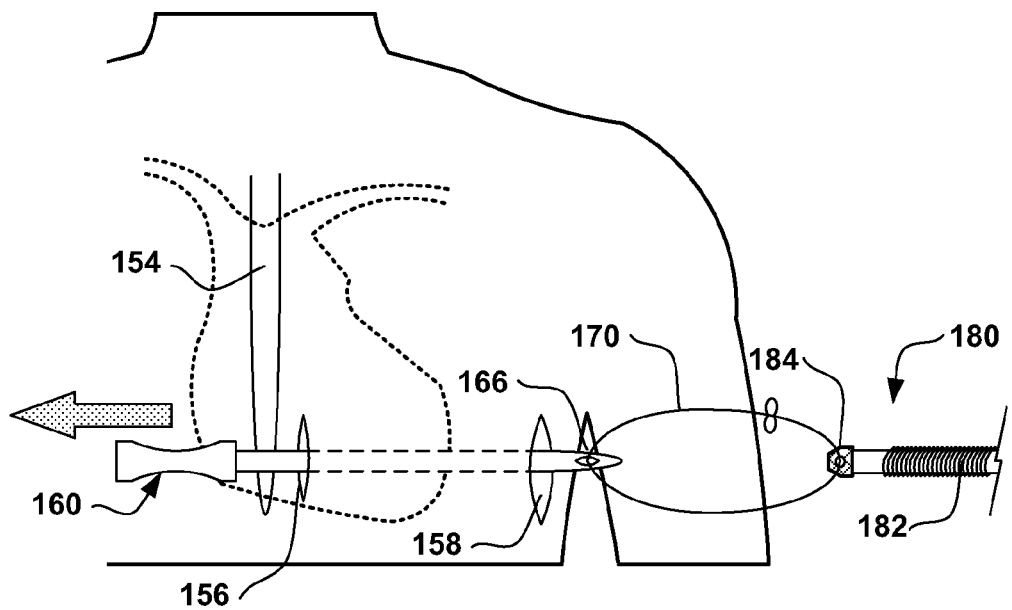

As shown by the arrow in FIG. 7, the insertion tool 160 is inserted through the xiphoid incision 156 and advanced toward the axillary incision 158. As shown in FIG. 8, a lead 180 is prepared for use, with the lead 180 including an attachment feature 184 and at least one electrode 182. The insertion tool 160 is inserted until its distal tip, including the attachment feature 166, can be accessed through the axillary incision 158. Then a suture 170 is used to attach the attachment feature 166 of the insertion tool 160 to attachment feature 184 on the lead 180.

Figure 9:
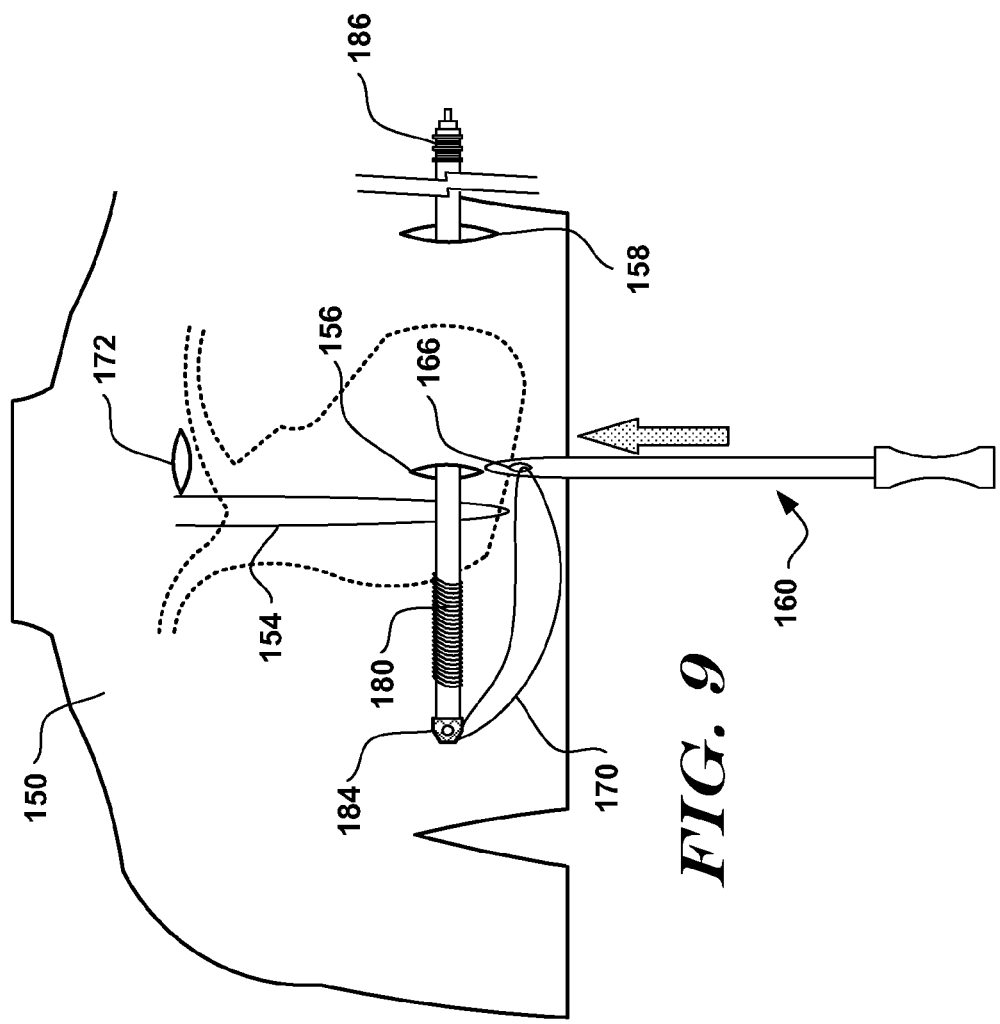

Next, the insertion tool 160 is withdrawn through the xiphoid incision 156, with the suture 170 pulling the lead 180 into the patient's subcutaneous tissue through the axillary incision 158. The end of this pulling step is shown in FIG. 9, where the attachment feature 184 at the distal end of the lead 180 extends through the xiphoid incision 156. At the end of this step, the proximal plug 186 of the lead 180 may be located relatively near the axillary incision 158, though this may depend on the anatomy of the patient 150 and the length of the lead 180.

In the example shown, the suture 170 remains attached to the insertion tool 160, which is shown in alignment with the sternum 154 in preparation for the next step of the procedure. An upper incision 172 is made a short distance to the left of the sternum 154 at a location that is superior to the xiphoid incision 156, approximately along the left sternal margin. For example, the upper incision 172 may be located approximately 8 to 18 cm superior of the xiphoid incision 156, and 1-3 cm left of the sternum 154. The upper incision 172 may also be described as level with or inferior to the manubrium and/or level with or superior to the atria of the heart. These particular locations are illustrative and not required; various implant locations can be used as described above relative to FIG. 1.

Figure 10:
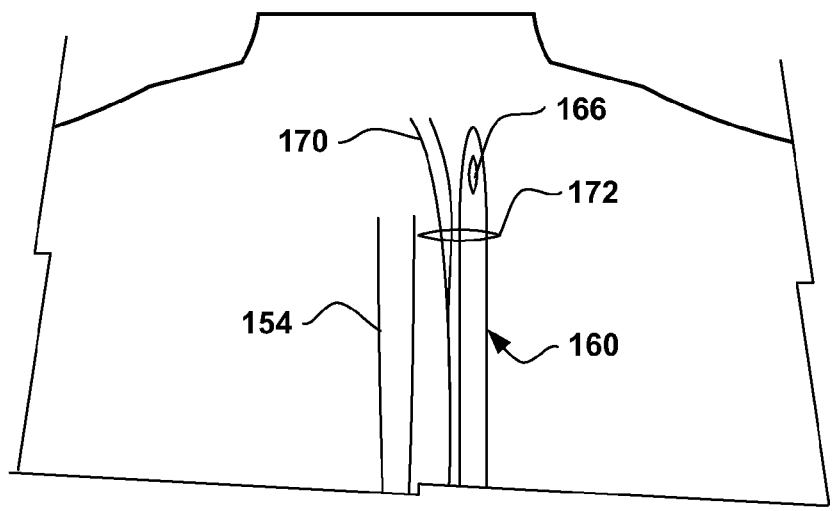
Figure 11:
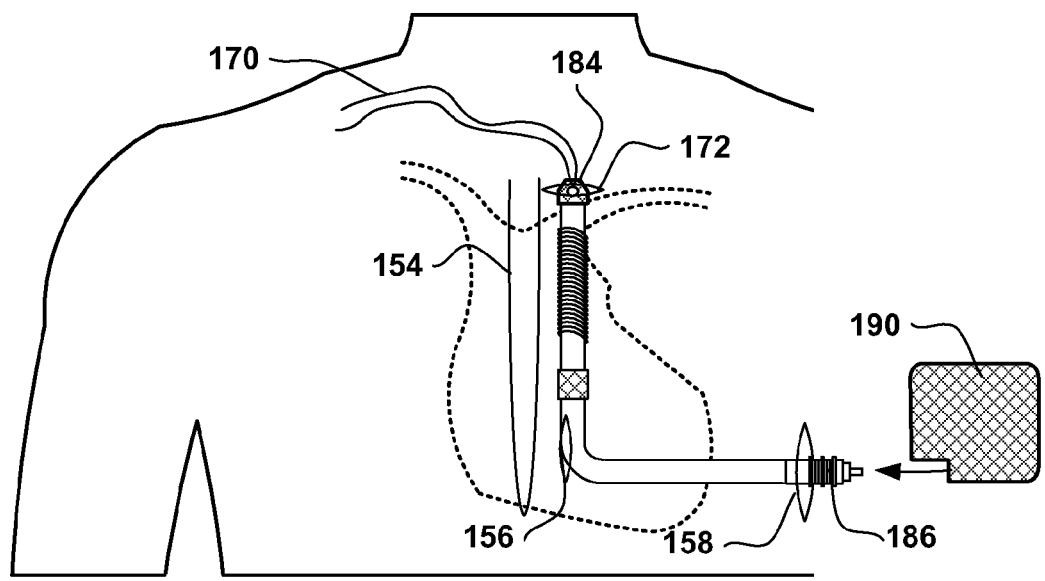

Next, the insertion tool 160 is reinserted into the xiphoid incision and advanced generally parallel to the sternum 154 toward and through the upper incision 172. The step ends as shown in FIG. 10, when the distal tip of the insertion tool 160 extends out of the upper incision 172 until the attachment feature 166 can be accessed. Next, a forceps (not shown) is used to grasp the suture 170, which is cut from the attachment feature 166. The insertion tool 160 is withdrawn. The forceps (not shown) is used to pull the suture 170 through the upper incision 172, drawing the distal end of the lead 180 through the xiphoid incision 156 into the patient and through the tunnel formed by the insertion tool 160. The suture 170 is pulled until the lead 180 achieves the position shown in FIG. 11, where the distal tip of the lead 180 and its attachment feature 182 can be accessed at the upper incision 172.

The Cameron Health, Inc. S-ICD® system has been implanted in a number of patients in the United States, Europe and New Zealand using methods generally as shown in FIGS. 7-11. In some such procedures, the attachment feature 184 of the lead would then be sutured to patient tissue at the upper incision 172, and a suture sleeve would be added at the xiphoid incision, while the proximal end 186 of the lead 180 would be attached to a canister 190. The canister 190 is then implanted through the axillary incision 158 and sutured to the patient tissue as well.

Several modifications to the method already in use are provided by the alternative structures for leads and/or suture attachment features shown herein. In various embodiments disclosed herein, additional steps/features are provided in the method shown, for example:

In one example, the lead 180 may take the form shown in FIGS. 3A-3C, with a suture sleeve provided adjacent the upper incision 172 and, optionally, taking on the moveability characteristics described above.

In another example, the lead 180 may take the form shown in FIGS. 5A-5D. During the placement of the lead, the wings would be kept in the configuration of FIG. 5B. Once drawn into the desired position the wings would be unwrapped/extended and then sutured to subcutaneous tissue near the upper incision in a configuration shown by either FIG. 5A or FIG. 5C. The lead 180 may also be as in FIG. 5D, with a mesh that is unwrapped once in place and then sutured to subcutaneous tissue.

In another example, the lead 180 may take the form shown in FIGS. 6A-6C, with the attachment features of the arms used during the implantation step for securing the lead to the insertion tool. After the lead is generally in place, the suture attachment to the insertion tool would be removed. Next, the flexible arms at the distal end of the lead would be spread away from the axis of the lead and secured to patient tissue.

Figure 12A:
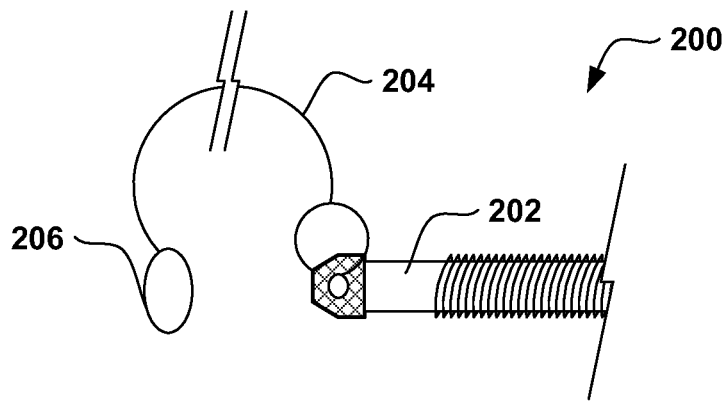
FIGS. 12A-12B show an illustrative lead pre-loaded with a suture for implantation.
Figure 12B:
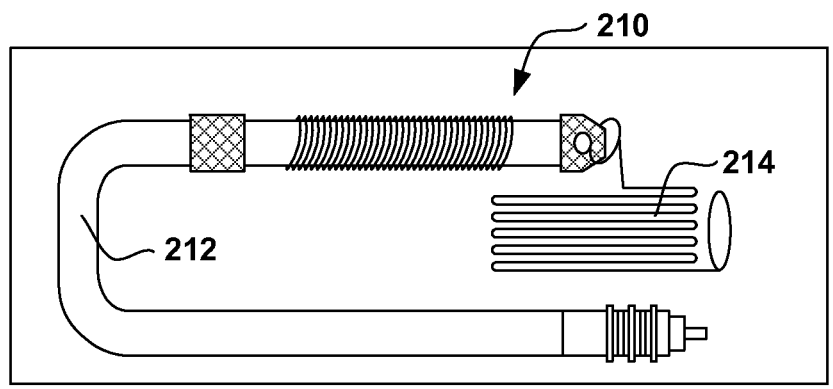

FIGS. 12A-12B show an illustrative lead pre-loaded with a suture for implantation. As shown at 200, a lead 202 is shown with a distal end that is coupled to a suture 204 which in turn includes a loop 206. These may be pre-loaded before packaging and/or sterilization for convenience. The suture 204 may be any structure having biocompatibility, flexibility and strength allowing it to be used during any of the implant procedures shown herein. Turning to FIG. 12B, a sterile package 210 may be used for shipping a lead 212 having a preloaded suture 214 for use in implantation.

Figure 13:
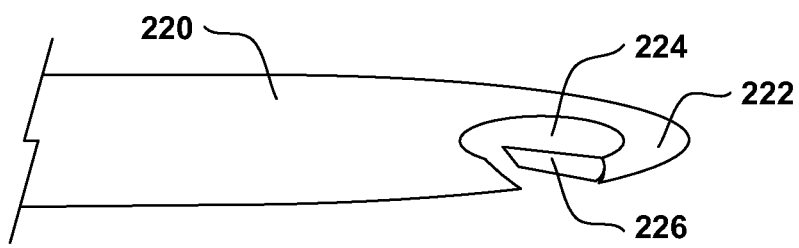
FIG. 13 illustrates the distal end of an example insertion tool.

FIG. 13 illustrates the distal end of an example insertion tool 220. While the insertion tool shown, for example, in FIGS. 7-11 has a simple suture hole at its dissecting tip as an attachment feature, the design shown in FIG. 13 includes an additional feature. In the example of FIG. 13, a distal end 222 has a bullet-shape that enables dissection through subcutaneous tissue while having a blunt tip that will not easily pierce the skin. A suture opening is shown at 224 and access thereto is controlled by a moveable element 226 which can allow entry of a loop (for example loop 206 shown in FIG. 12A) but prevents ready exit of the loop. The insertion tool 220 may be useful if a suture is preloaded on the electrode with a loop as shown in FIGS. 12A-12B. The loop of the suture would be passed by the moveable element 226 into the suture opening 224 and then prevented from escaping the suture opening 224 by the moveable element. The combination of lead with a preloaded suture and the insertion tool 220 may simplify portions of the implant procedure shown above in FIGS. 7-11 by reducing the amount of knot-tying required. This structure/plan may also be used in association with an embodiment shown in FIGS. 16-21, below, in which the proximal plug cover 330 (FIG. 17) would come preloaded with a suture. If so desired, rather than having a suture connecting the lead to the insertion tool 220, the hook-shape of the distal end of the insertion tool 220 may directly capture an attachment feature of an implantable lead. In some embodiments, the moveable element 226 is spring loaded; in another example, a manipulation switch or trigger can be placed at the proximal end of the insertion tool 220 to allow control over the moveable element 226.

Figure 14:
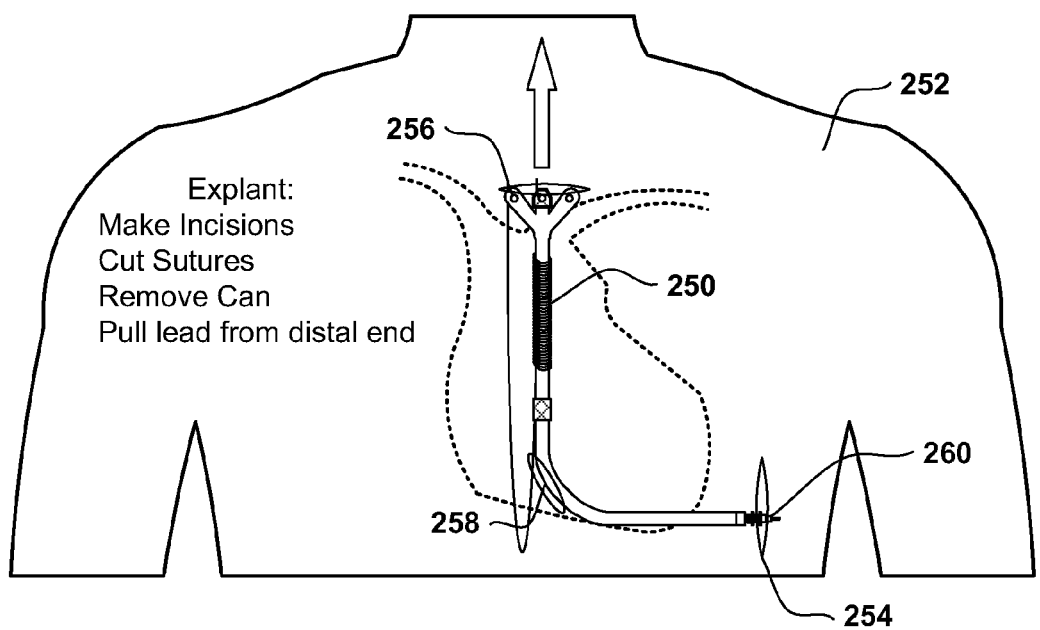
FIG. 14 shows and details some steps for explanation of certain lead embodiments.

FIG. 14 provides an illustration of removal of certain lead embodiments. In the embodiment shown, a lead 250 is to be extracted from patient 252. The procedure may begin by making an incision at 254 and removing the canister (not shown—see FIG. 1 at 12). This step has been completed in the step as shown, such that the lead 250 is exposed at its proximal end 260 and is no longer connected to the canister.

In the example shown, the lead 250 includes an anchoring-type structure at its distal end, near an upper incision shown at 256. As a result, the lead 250 has a larger structure at its distal tip than at its proximal end 260. Pulling the lead from its proximal end at 260 would be difficult for this example because the anchoring structure would have to be pulled a significant distance through the subcutaneous tissue. Instead, an incision is made at 256 and the lead 250 can be pulled from its distal end to remove it. This process will draw the proximal end 260 through the subcutaneous tissue. An alternative may include slicing the lead near the anchoring structure 256 to separate the generally cylindrical portion of the lead 250 from the anchoring structure 256.

Optionally, as shown, an incision may also be made at an intermediate location, such as a xiphoid location as shown at 258, to ease the explant procedure. For example, in some embodiments having an implant configuration as shown, a suture sleeve may be placed on the lead at or near the xiphoid of the patient to provide an additional anchoring structure. The xiphoid incision 258 allows removal of the suture sleeve, if any, and also allows pulling force and control to be applied at the location of a bend in the lead 250. In another example, the lead 250 may be cut into two pieces at the xiphoid incision 258 and removed from each end or entirely through the xiphoid incision. In one illustration, the lead 250 undergoes curing/hardening to retain a specific curvature near the xiphoid incision, making the lead 250 difficult to remove from either end, so cutting lead 250 into pieces may ease the explant procedure.

Figure 15:
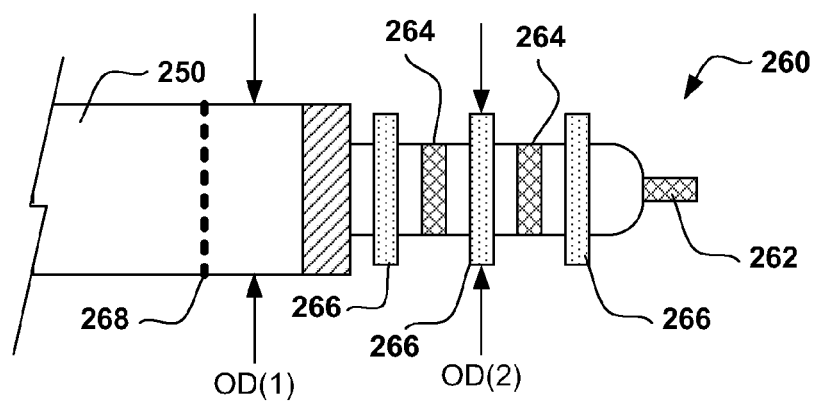
FIG. 15 shows details for an example implantable lead.

FIG. 15 shows details for an example implantable lead adapted for the explantation shown in FIG. 14. In the example shown, the lead 250 includes a plug assembly having several conductive rings 264 and a proximal wire connector 262 that allow for conductive coupling between the electronics of the system and the electrodes on the lead 250. A number of seals 266 separate the conductive rings 264 from one another and the proximal wire connector 262. Easy passage of this proximal end of the lead 250 through tissue may be ensured by having the outer diameter of the lead, OD(1), be equal to or greater than the outer diameter of the seals, OD(2). This would allow removal without destroying the plug assembly 260 or removing it from the lead. As an alternative, as highlighted at 268, one could simply cut the proximal end of the lead 250 before explanation. This may be desirable for some cases where the plug 260 cannot be readily separated from the canister due to aging or due to permanent attachment. In another alternative, the seals 266 are flexible to allow atraumatic flexing during removal as the plug assembly 260 passes through subcutaneous tissue. In another alternative, a cap may be attached over the proximal end 260 during removal.

FIGS. 16-21 show another illustrative method of implanting a subcutaneous cardiac device. Beginning with FIG. 16, a system is to be implanted in patient 300. The procedure uses three incisions: an upper incision at 302, located superior of the ventricles of the heart and level with or inferior to the manubrium, generally alongside the sternum; a xiphoid incision 304 generally superior and to the left of the xiphoid; and an axillary incision 306 generally located near the left axilla of the patient, possibly along or just inferior to the inframammary crease, and over the ribs.

An insertion tool 310 is used, including a tunneling portion 312 and a distal attachment feature 314, shown as a suture opening. The insertion tool 310 is inserted through the xiphoid incision 304 and advanced over the sternum to the upper incision 302. Next, the insertion tool 310 is connected via a suture 320 at its attachment feature 314 to a proximal plug cap 330 having an attachment feature 332, wherein the proximal plug cap 330 is attached to lead 340. As shown in the detail view of FIG. 17, the proximal plug cap 330 with attachment feature 332 fits over the proximal plug 344 for the lead 340. This attachment of the proximal plug cap 330 to the lead 340 may be secured by interference fit, screw, suture tying or tightening, or by any other suitable method/structure.

In an alternative embodiment, the proximal end/plug 344 may simply contain an attachment feature such as a suture opening, hook or the like, which may be used both during implantation and also during attachment to the system canister, which is often performed with a set screw but which could also be performed with a pin, suture, wire or other structure that would pass through or couple with an attachment feature on the plug 344. The plug cap may protect the proximal end of the lead 340 if needed. If desired, the system may be designed to tolerate attachment of the plug 344 to a header even after the plug 344 has been exposed to bodily fluids, so the plug cap 330 can be omitted.

Once the insertion tool 310 is attached to the lead 340 it is then drawn back out of the xiphoid incision 304, so that the tool 310 pulls the lead 340 into subcutaneous tissue of the patient 300 through the upper incision 302 using suture 320. One reason for performing the method as shown in FIG. 16 may be the inclusion of an anchoring element 342 on the lead 340 which has a larger profile than the rest of the lead 340. By pulling from the proximal end of the lead 340, the tunnel needed to pull the lead 340 into place can be smaller than what would be needed to pass the distal anchoring element 342.

Figure 18:
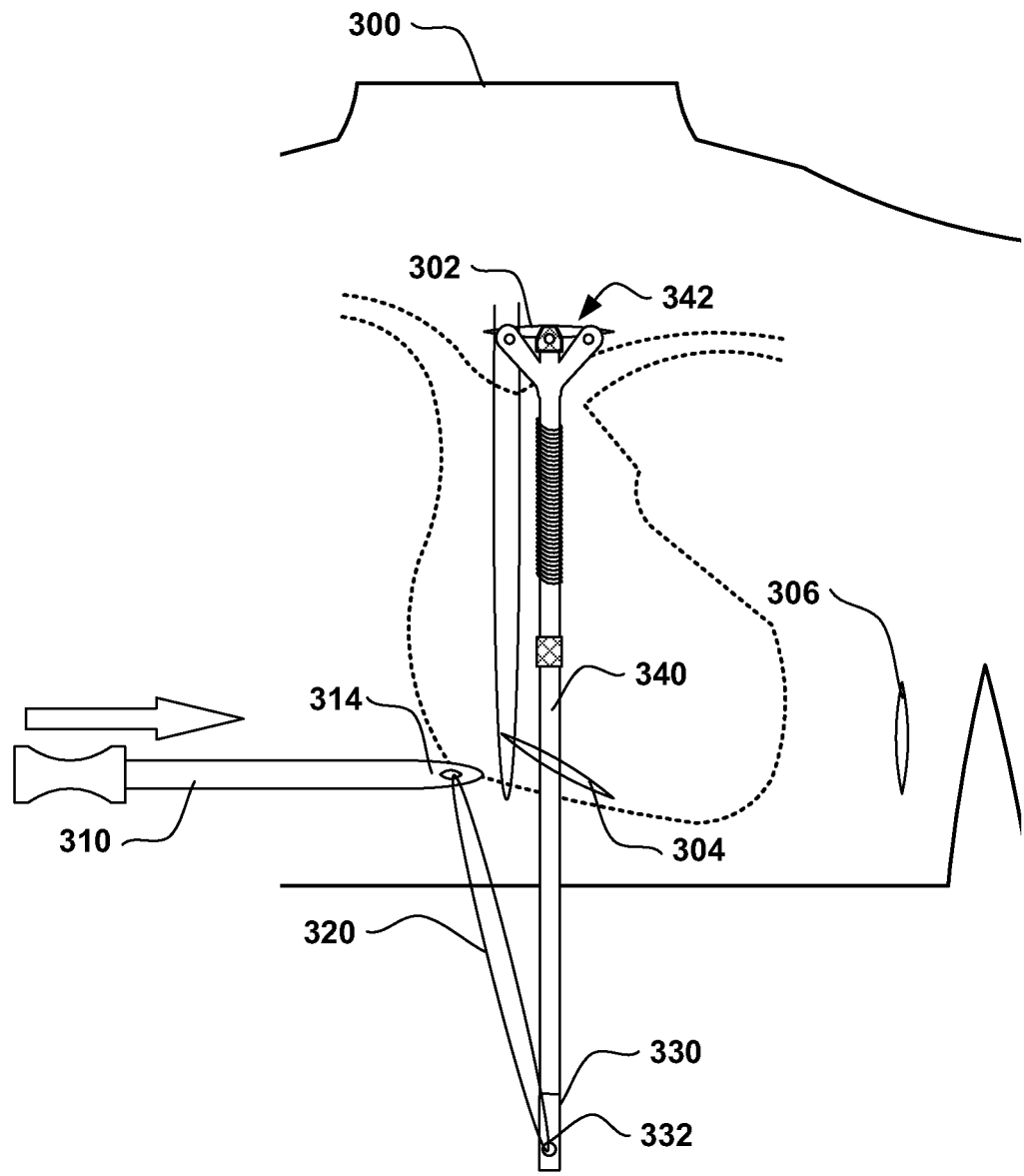

Turning to FIG. 18, the lead 340 is pulled through the xiphoid incision 304 until the distal anchoring structure 342 reaches the upper incision 302. Since the anchoring structure 342 has a larger profile than the rest of the lead 340, it remains in place at the upper incision 302 and will not readily pass farther down the subcutaneous tunnel. If desired, the anchoring structure 342 may also be sutured, adhered or stapled to the subcutaneous tissue near the upper incision 302.

Next, as suggested by the alignment of the insertion tool 310, the insertion tool 310 will be passed into the xiphoid incision 304 and directed toward the axillary incision 306. During this step, the suture 320 remains attached to the attachment feature 314 on the insertion tool 310 as well as the attachment feature 332 of the proximal plug cap 330 on the lead 340.

Figure 19:
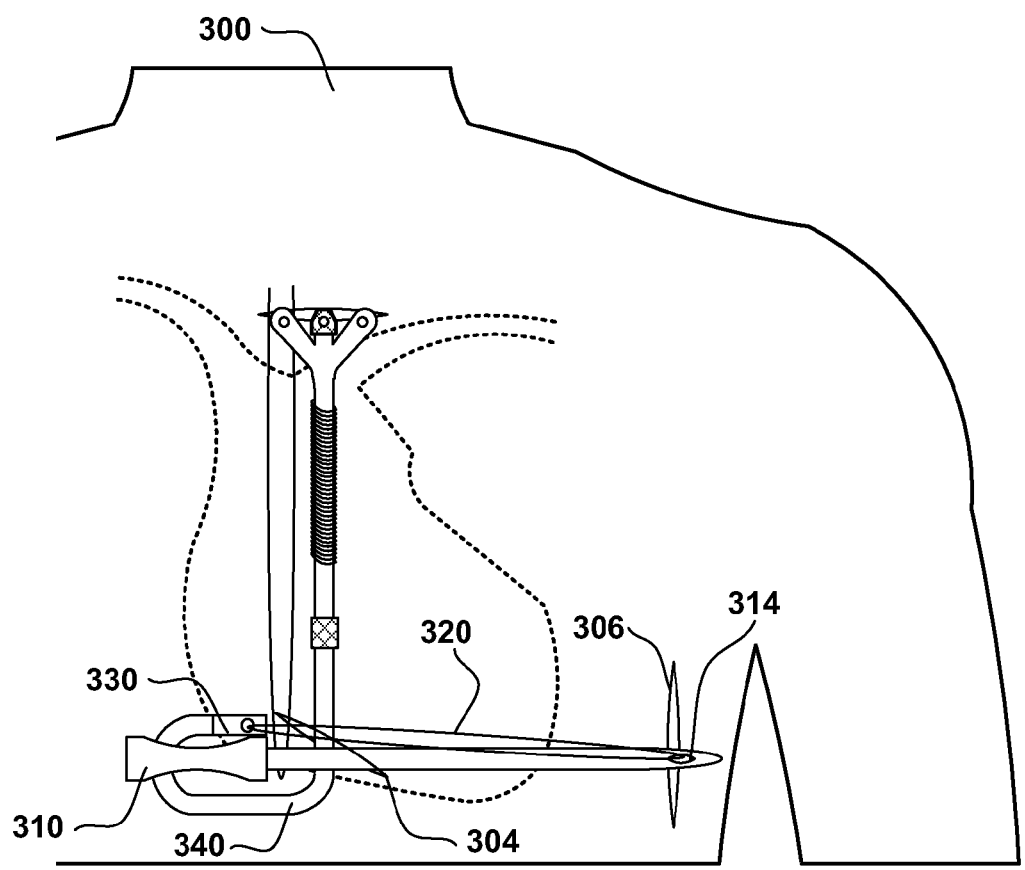

Turning to FIG. 19, as the insertion tool 310 passes through the xiphoid incision 304 to and out of the axillary incision 306, the lead 340 bends around to draw its proximal end and the proximal plug cap 330 near to the xiphoid incision 304. The insertion tool 310 is advanced until the attachment feature 314 can be accessed at the axillary incision 306. Next, the suture 320 is grasped with a forceps (not shown) and cut. The insertion tool 310 is then removed.

Figure 20:
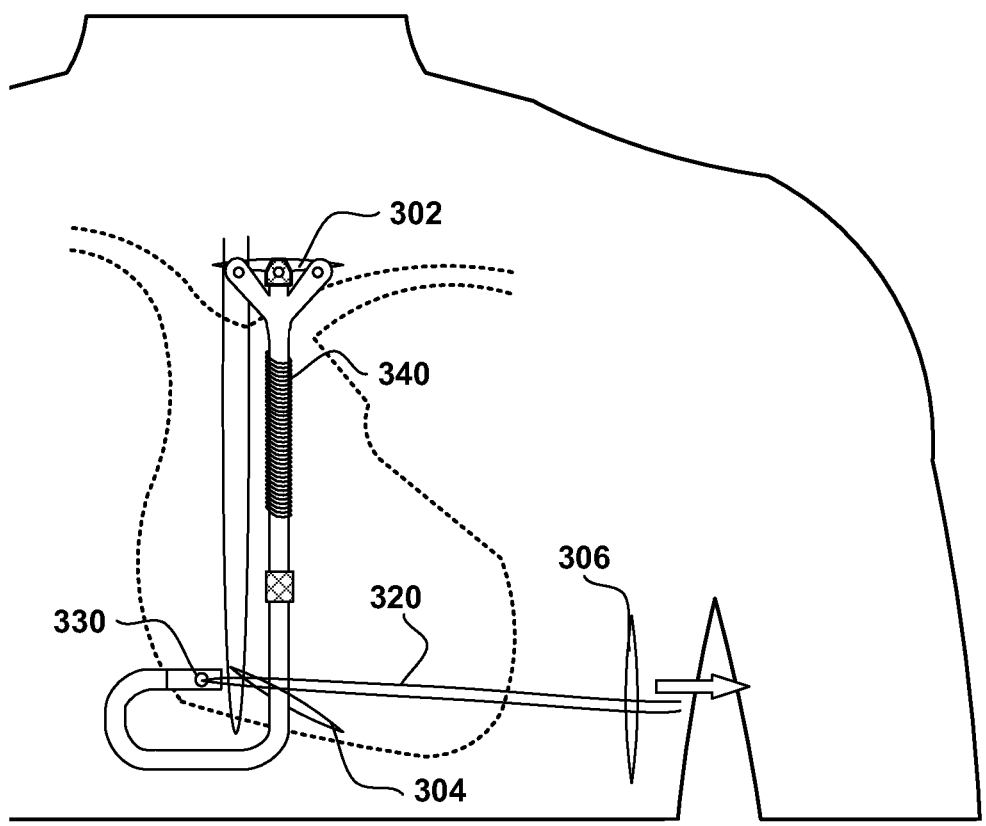
Figure 21:
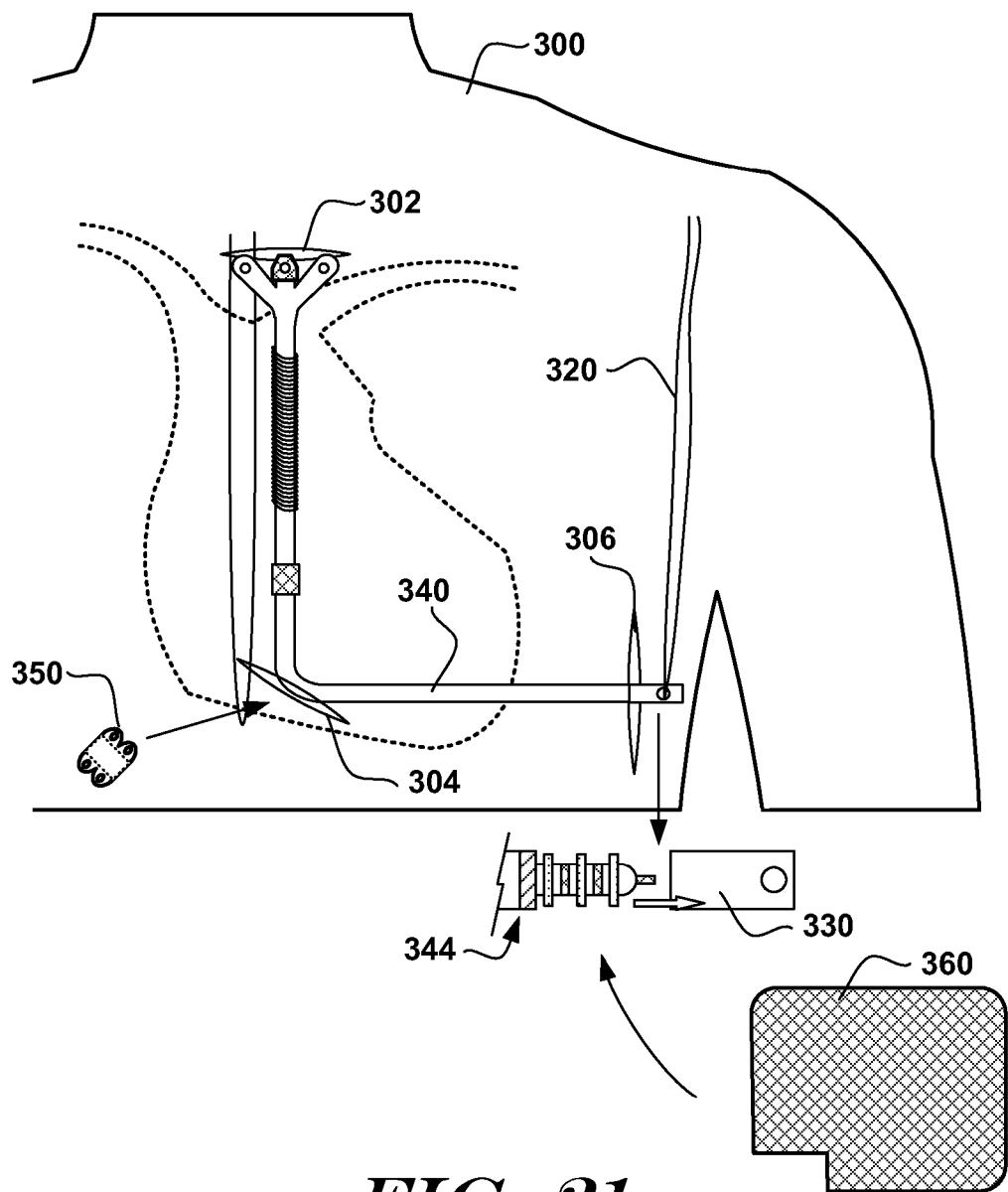

Turning to FIG. 20, after the insertion tool 310 is removed, the suture 320 is pulled out through the axillary incision 306. As the suture 320 is pulled, it draws the lead 340 into the subcutaneous tunnel formed by the insertion tool between the xiphoid incision 304 and the axillary incision 306. A distal portion of the lead 340 remains in place in the subcutaneous tunnel between the xiphoid incision 304 and the upper incision 302. Completion of the lead insertion is shown in FIG. 21, with the suture 320 pulled such that the proximal plug cap 330 can be accessed at the axillary incision 306. A suture sleeve 350 may be applied on the lead 340 at any of the incisions 302, 304, 306, particularly at either the axillary incision 306 or, as shown, at the xiphoid incision 304. At the end of the procedure, the lead 340 no longer sticks out of the upper incision 302 and the xiphoid incision 304.

Next, as shown in the detail view, the proximal plug cap 330 can be removed from the plug 344, which can be inserted in and attached to the canister 360. Blunt dissection is used to establish a pocket adjacent the axillary incision 306 for receiving the canister 360; in one example the pocket extends generally toward the mid-axillary line. The canister 360 is inserted into the subcutaneous tissue of the patient 300 via the axillary incision 306. The incisions 302, 304, 306 can then be closed using standard surgical techniques. System testing, power-up and/or initialization can be performed before the incisions are closed to allow replacement, removal or repositioning, as needed.

Figure 22A:
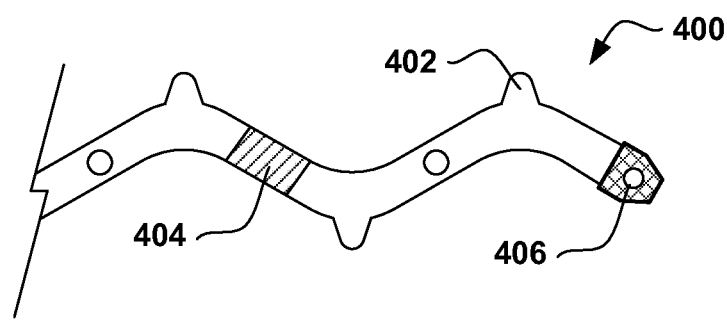
FIGS. 22A-22C show structures for encouraging tissue anchoring of an implantable lead.
Figure 22B:
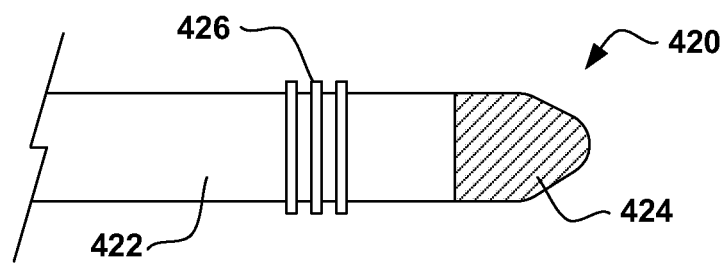
Figure 22C:
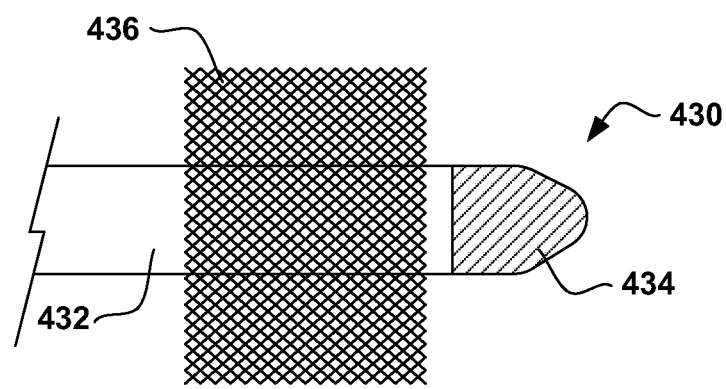

FIGS. 22A-22C show structures for encouraging tissue anchoring of an implantable lead. Each structure in FIGS. 22A-22C is designed to encourage or make more secure tissue ingrowth for a subcutaneous lead system. In FIG. 22A, a lead 400 includes a number of small nubs 402 extending out from the surface of the lead 400 among electrodes 404, 406. The small nubs 402 may allow adjacent subcutaneous tissue to grow in/around the lead 400 in a manner that holds the lead 400 in place. In some examples, the lead is designed to hold the wavy shape shown as well, for example, by thermoforming or curing the material of the lead. In some examples the region of the nubs 402 and/or the nubs themselves are roughened to encourage tissue attachment or provided with a steroid coating.

In FIG. 22B, the lead 420 is shown having a lead body 422 and a distal tip electrode 424. A number of rings 426 are provided around the lead body 422 to encourage tissue ingrowth. In some examples, the rings 426 and/or a section of the lead 422 may be formed of a material such as silicone that is not considered highly lubricious in contrast, for example to materials such as polytetrafluoroethylene, to increase the stickiness of the lead in tissue.

In FIG. 22C, the lead 430 is shown having a lead body 432 and a distal tip electrode 434 with a porous or mesh region 436. Porous or mesh structures can be provided to encourage tissue ingrowth. If desired, substances such as steroids may be provided on the lead body 432 to encourage tissue growth, including at or near the porous or mesh region 436 or on the mesh 436 itself.

Figure 23A:
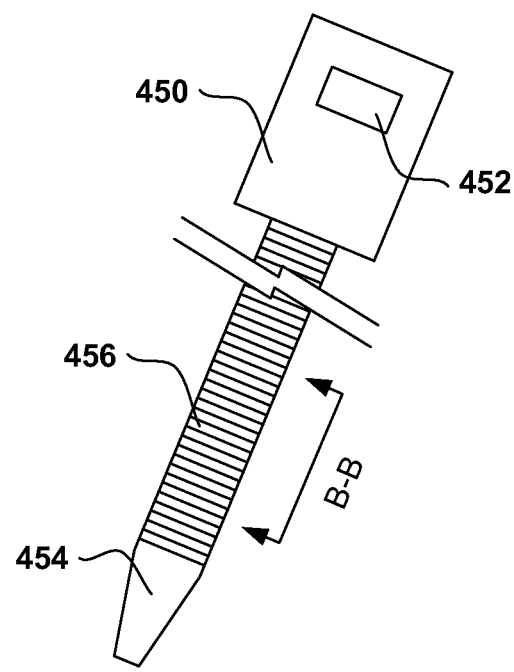
FIGS. 23A-23B illustrate an alternative to sutures for coupling together elements of an implantable system.
Figure 23B:
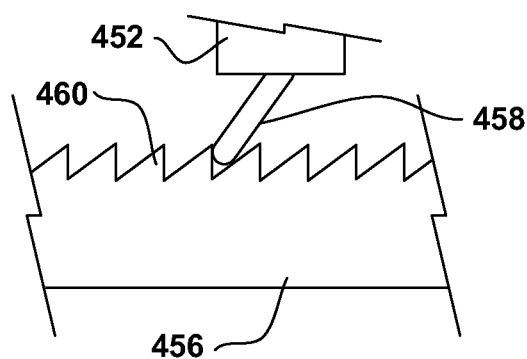

FIGS. 23A-23B illustrate an alternative to sutures for coupling together elements of an implantable system. Here a "zip tie" type of structure is shown. In FIG. 23A, the coupler 450 includes a slot 452 at one end and a tip 454 at another end, with a zip structure 456 therebetween. The tip 454 can be passed through the slot 452, which includes a flap that engages the zip structure 456. FIG. 23B shows a cutaway view with the zip structure 456 passing through the slot 452. As highlighted in FIG. 23B, the flap 458 allows one way passage of the zip structure 456, which includes teeth 460, through the slot 452.

FIGS. 24A-24E demonstrate reusable subcutaneous anchoring structures. FIG. 24A shows the reusable structure 500 including a number of arms 502 each including an attachment feature 504 (shown as a suture hole, but again replaceable with a pierce-able region). A mesh 506 may also be provided as backing for the anchoring structure, and the arms 502 can be omitted if desired and the mesh used for suture attachment instead. The arms 502 spread outward from a center section that includes lead coupling elements 508 having openings as shown. As shown in the side view of FIG. 24B, the lead coupling elements 508 are flexible and able to be curled upward to define a channel 510 for receiving a lead, over the backing 506.

FIG. 24C shows the reusable anchoring structure 500 of FIGS. 24A-24B receiving a lead 520. The lead 520 is placed in the channel between the lead coupling elements 508 such that an opening in the lead 520 is aligned with the openings of the lead coupling elements 508. The opening in the lead 520 is shown between a proximal electrode 522 and a distal electrode 524; a different location, including at the distal tip of the lead 520 or more proximal than either electrode 522, 524 may be used instead.

A coupler 512 as shown in FIGS. 23A-23B is inserted through the aligned opening of the lead 520 and the openings of the lead coupling elements 508 to attach lead 520 to the anchoring structure 500. The tip of the coupler 512 is then inserted through the coupler slot and tightened to hold the lead 520 in place relative to the anchoring structure 500. For removal, the coupler 512 can be cut and removed, and the lead 520 can be removed leaving the anchoring structure 500 in place. A different lead may then be placed and secured to the anchoring structure 500 in similar fashion. Use of the coupler 512 is optional; a suture or other securing element may be used instead.

FIG. 24D shows another alternative. Here, an incision 550 is made over the ribs 552 of the patient (the ribs 552 are shown for illustration; in an actual surgery there may be fascia or other tissue that would cover the ribs so they may not be so easily viewed as in the Figure). A screw 560 is provided having an attachment feature 562. The screw may take the form of a bone screw, which can attach to the ribs 552 themselves. In another embodiment, the screw 550 is configured to attach through the fascia (not shown) and into the cartilage between the ribs 552. In use, the screw 560 is emplaced through the incision 550, and a lead is tunneled through tunnel 554 to the area of the incision 550 either before or after the screw 560 is placed. The lead (not shown) can then be anchored in the patient by attachment to the screw 560. An alternative screw design is shown at 564, this time including a stopper 566 to prevent over-penetration of tissue. The stopper 566 may include ridges or nubs on its outer edge or as shown at 568 to prevent it from twisting further or backing out once it is emplaced.

FIG. 24E shows another alternative. Again an incision is made as shown at 550 over the ribs 552 of a patient, and a tunnel 554 is shown in phantom indicating that a lead can be tunneled to the area of the incision 550. A patch 570 formed of a mesh material (or a solid sheet, in an alternative) is placed in the area of the incision 550. The patch 570 is designed for attachment to the subcutaneous tissue and will remain in place permanently while allowing easier suturing to the patch 570 as compared to suturing to the fascia. The patch 570 may provide easier verification that sutures are well anchored, since the patch 570 may be colored or patterned in a way to make it easy to see where the suture passes through it for example by making the patch bright green, black or some other non-tissue/non-fascia color. The patch 570 may include or may be placed using tissue adhesive.

In some embodiments the patch 570 is permanent and may be made using various polymers including polypropylene, polyethylene, polyester methylmethacrylate, mersilene, silicone, and, in one example, polytetrafluoroethylene. Dacron® or Teflon® are brand names for certain possible materials. In another example, the patch 570 may be made using biodegradable substances including, for example, polyglycolic acid, polylactic acid, or copolymers thereof, which would render the patch 570 more of a temporary anchoring structure, with the expectation that a lead, once emplaced may include structures or materials encouraging tissue ingrowth such that the patch 570 would become unnecessary after the acute healing phase is complete. Other materials may be used as desired. The patch 570 may be similar to a hernia patch or mesh. Rather than attaching to the patch 570 by piercing with a suture, the patch 570 may include a loop or loops of material for attachment to a lead.

Figure 25A:
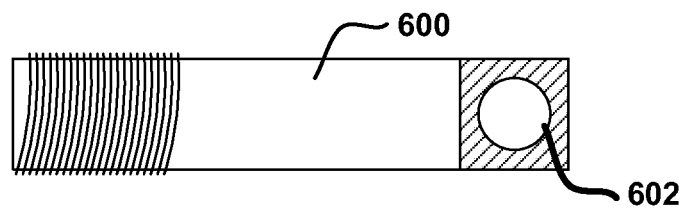
FIGS. 25A-25C illustrate details of a snap-on lead anchoring structure.
Figure 25B:
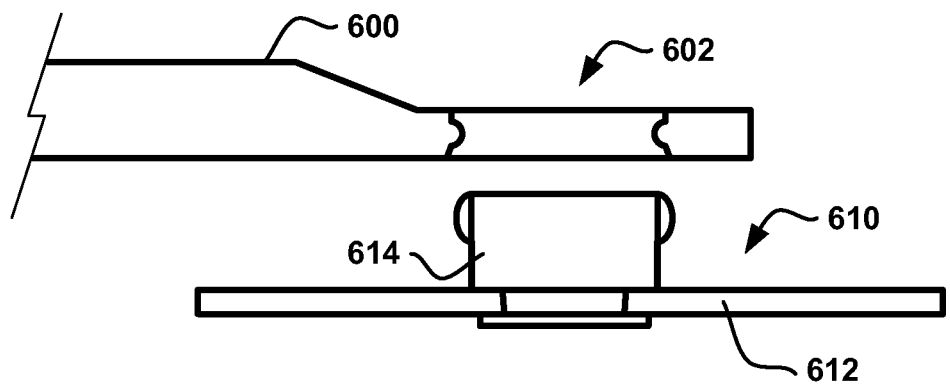
Figure 25C:
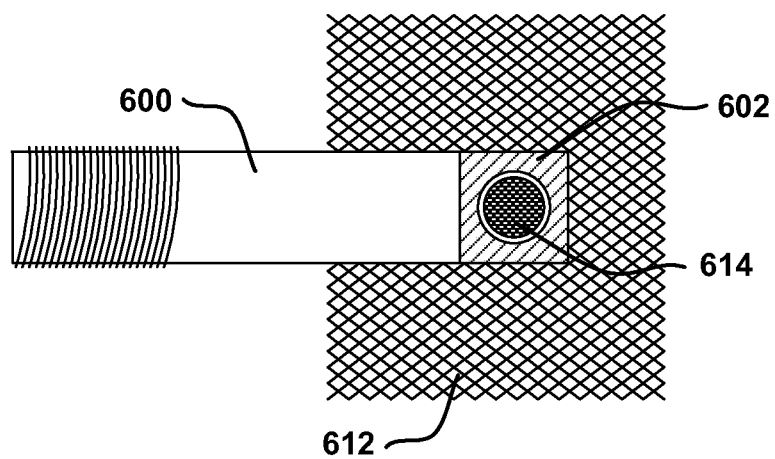

FIGS. 25A-25C illustrate details of a snap-on lead anchoring structure. FIG. 25A illustrates a lead 600 having an attachment opening 602 which may be formed as the female half of a snap fastener. As shown in FIG. 25B, an implantable anchoring structure 610 includes a backing layer 612 and a corresponding male half 614 of a snap fastener. As shown in FIG. 25C, the lead 600 is anchored by snap attachment between elements 602 and 614, and the backing layer 612 may take the form of a mesh or sheet of material to which element 614 is attached. The attachment opening 602 and male half 614 comprise mating structures for a snap fit attachment.

An attachment opening 602 may allow access to ensure a correct snap-fit is achieved, and also may be used during removal to press against the anchoring structure 610 while lifting the lead 600. In an alternative, a cap may be provided over opening 602 to prevent the male half 614 from piercing or irritating the skin of the patient. A thru-hole may be provided to receive a suture or a pin to prevent release of the snap fit.

Figure 26A:
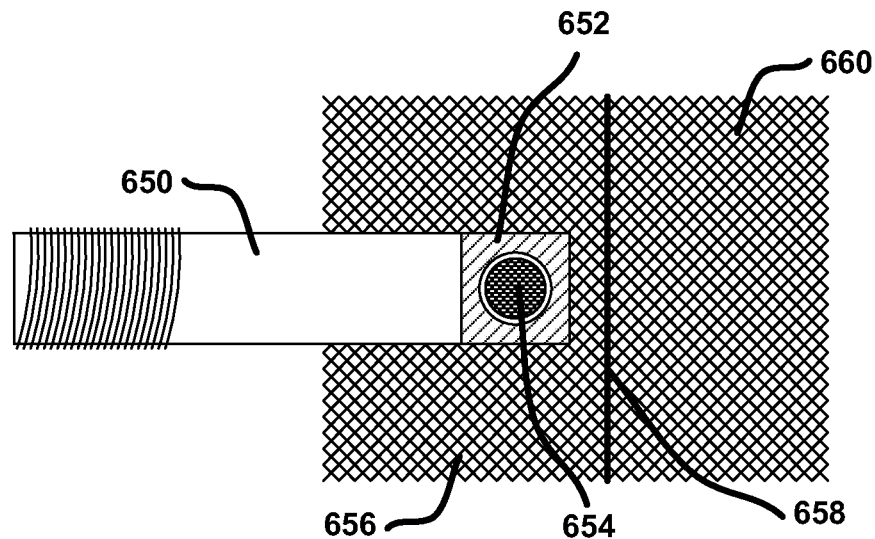
FIGS. 26A-26B show a fold-over anchoring structure.
Figure 26B:
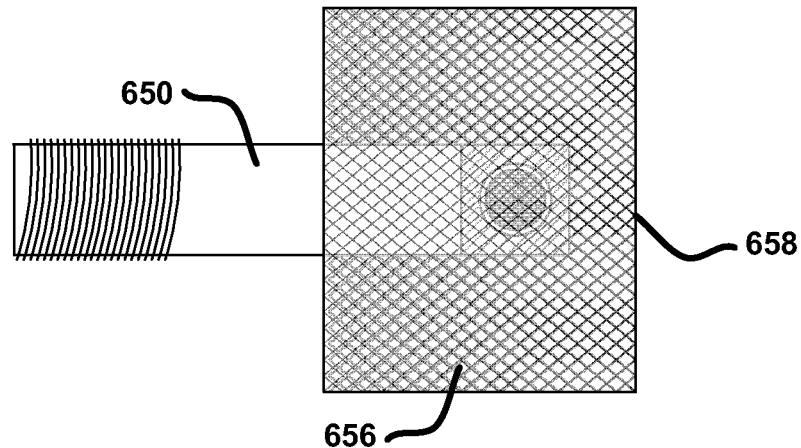

FIGS. 26A-26B show a fold-over anchoring structure. Here the attachment feature is again shown as the snap fastener of FIGS. 25A-25C, with lead 650 and snap structure 652, 654, with element 654 attached to backing layer 656. In other embodiments, a suture attachment or clip attachment may be used instead. The purpose of the embodiment in FIGS. 26A-26B is to show a folding line 658 which allows cover portion 660 to be folded over the attachment structures 652, 654, as shown in FIG. 26B. By folding over the backing layer 656, the attachment features are not allowed to irritate or pierce through the skin of the patient and/or to find their way through an adjacent incision during the healing process. Particularly for embodiments using implantable sutures to make the attachment, it is possible sometimes for the suture that attaches a lead to an anchoring structure to make its way to and through the incision before healing is complete, adding to a risk of infection. A cover that folds over as shown in FIGS. 26A-26B can prevent this migration of the suture. The fold over-cover, or simply mesh as a cover, may be used in any of the embodiments shown herein.

For any of the implant structures shown, anti-microbial, antibiotic, pro-ingrowth or other coatings may be provided to assist in preventing infections. For example, given the desire to cause stronger fixation to tissue, a pro-tissue-growth coating such as a steroid or other composition may be applied to the permanent implant structures. In addition, the leads, sutures and/or clips (if used) may have such pro-tissue-growth coatings or compositions applied as well.

In addition to possibly UV curing the arms of the lead 100 in FIG. 5A, the location of the curvature of the lead at approximately the xiphoid in FIG. 1 may also include UV curable characteristics. This would allow the lead shape/curve to be set by curing during implantation, making it difficult for the lead to migrate. For such an example, rather than removing the lead via the proximal or distal end thereof, one may remove the lead by withdrawing it at approximately the xiphoid incision. UV curable material could also be used in the embodiment shown in FIGS. 6A-6C, or in any other embodiment in which the lead has a lower profile during implant and is then expanded, reshaped, modified, bent, etc. to a different shape to create fixation. When referring to a curable material herein, this may include a material curable using ultraviolet or other light source, or curable through heat or application of a curing substance. In one example, a UV curable material, such as a polyurethane oligomer mixture that can be cross-linked through UV curing, or other materials that can be polymerized by UV curing including acrylate monomers, urethane crylate oligomers and/or acrylamides, may be encapsuled by other materials to ensure biocompatibility. The UV curable material may be provided in mesh or solid form, for example, a plurality of curable fibers may be provided. Heat-curable materials may be used instead, again using either solid or mesh forms. In yet another example, a shape memory material can be used as part of the structure, with an activation temperature near body temperature to provide added rigidity during implant.

Several embodiments refer to a "suture" as being used for attaching a lead to an insertion tool. This may include those structures commercially sold as sutures, for example, those made of natural material such as silk and/or synthetic materials such as polyglycolic acid, polylactic acid, and polydioxanone, each of which are known for use as absorbable sutures, and/or nylon and polypropylene, which are typically non-absorbable. Various coatings, including anti-microbial, anti-wicking or lubricious coatings may be applied as well. Further, as used herein, "suture" indicates any item that can be used to couple together objects in a surgical environment. "Suture" may include flexible metal structures or any other material that is sufficiently biocompatible for use in a surgical procedure. A suture may be a monofilament or it may be a more complex structure including a braid, weave, winding, twisted thread, coated or multilayer member, etc. For purposes of anchoring a lead or implantable device in place, some practitioners may choose to avoid absorbable sutures, but this decision is by no means required in the context of the present invention.

The following U.S. Patents, U.S. Patent Application Publications, and U.S. Provisional applications are incorporated herein by reference as illustrative examples for design, operation and implantation of cardiac devices: U.S. Pat. No. 6,647,292, titled UNITARY SUBCUTANEOUS ONLY IMPLANTABLE CARDIOVERTER-DEFIBRILLATOR AND OPTIONAL PACER; U.S. Pat. No. 6,721,597, titled SUBCUTANEOUS ONLY IMPLANTABLE CARDIO-VERTER-DEFIBRILLATOR AND OPTIONAL PACER; U.S. Pat. No. 6,754,528, titled APPARATUS AND METHOD OF ARRHYTHMIA DETECTION IN A SUB-CUTANEOUS IMPLANTABLE CARDIOVERTER/DEFI-BRILLATOR; U.S. Pat. No. 7,149,575, titled SUBCUTA-NEOUS CARDIAC STIMULATOR DEVICE HAVING AN ANTERIORLY POSITIONED ELECTRODE; U.S. Pat. No. 7,330,757, titled METHOD FOR DISCRIMINATING BETWEEN VENTRICULAR AND SUPRAVENTRICU-LAR ARRHYTHMIAS; U.S. Pat. No. 7,248,921, titled METHOD AND DEVICES FOR PERFORMING CAR-DIAC WAVEFORM APPRAISAL; U.S. Pat. No. 7,392,085, titled MULTIPLE ELECTRODE VECTORS FOR IMPLANTABLE CARDIAC TREATMENT DEVICES; U.S. Pat. No. 7,655,014, titled APPARATUS AND METHOD FOR SUBCUTANEOUS ELECTRODE INSER-TION; U.S. Pat. No. 7,376,458, titled METHOD FOR DEFINING SIGNAL TEMPLATES IN IMPLANTABLE CARDIAC DEVICES; U.S. Pat. No. 7,477,935, titled METHOD AND APPARATUS FOR BEAT ALIGNMENT AND COMPARISON; U.S. Patent Application Publication Number 2006-0167503, titled METHOD FOR ADAPTING CHARGE INITIATION FOR AN IMPLANTABLE CAR-DIOVERTER-DEFIBRILLATOR; U.S. Patent Application Publication Number 2009-0228057, titled ACCURATE CARDIAC EVENT DETECTION IN AN IMPLANTABLE CARDIAC STIMULUS DEVICE; U.S. Patent Application Publication Number 2009-0259271, titled METHODS AND DEVICES FOR ACCURATELY CLASSIFYING CAR-DIAC ACTIVITY; U.S. Pat. No. 7,623,913, titled IMPLANTABLE MEDICAL DEVICES USING HEURIS-TIC FILTERING IN CARDIAC EVENT DETECTION; U.S. Pat. No. 7,623,909, titled IMPLANTABLE MEDICAL DEVICES AND PROGRAMMERS ADAPTED FOR SENSING VECTOR SELECTION; U.S. Patent Application Publication Number 2009-0036944, titled ELECTROMAG-NETIC INTERFERENCE SHIELDING IN AN IMPLANT-ABLE MEDICAL DEVICE; U.S. Patent Application Publication Number 2009-0198296, titled ADAPTIVE SHOCK DELIVERY IN AN IMPLANTABLE CARDIAC STIMU-LUS DEVICE; U.S. Patent Application Publication Number 2009-0187227, titled DATA MANIPULATION FOLLOW-ING DELIVERY OF A CARDIAC STIMULUS IN AN IMPLANTABLE CARDIAC STIMULUS DEVICE; U.S. Provisional Patent Application Ser. No. 61/221,316, titled CONFIRMATION OF TREATABLE ARRHYTHMIA IN IMPLANTABLE CARDIAC STIMULUS DEVICES; U.S. Provisional Patent Application Ser. No. 61/255,249, titled METHODS AND DEVICES FOR IDENTIFYING OVER-DETECTION OF CARDIAC SIGNALS; and U.S. Provi-sional Patent Application Ser. No. 61/255,253, titled ADAP-TIVE WAVEFORM APPRAISAL IN AN IMPLANTABLE CARDIAC SYSTEM. These patents and publications are incorporated for illustrative purposes as showing various characteristics of implantable cardiac stimulus systems, both directly in their disclosures and by virtue of references to other patents, applications and publications. The present invention may be used in other implantable systems as well, including cardiac monitoring systems.

The implanted systems can use any suitable technology for such aspects as the header connection, canister design, electronics, batteries, communication circuitry, antennae, etc. In one illustrative example, the canister contains opera-tional circuitry including input circuitry having passive filtering components, a sense vector selection switch array, one or more ECG amplifiers and analog-to-digital conver-sion circuitry. A microcontroller may receive signals from this input circuitry. Various battery chemistries can be used, such as one or several lithium-manganese-dioxide batteries. Illustrative output circuitry that can also be part of the operational circuitry may include an H-bridge system having multiple legs and high and low sides with high power switches that enable multi-phasic therapy delivery. Therapy may be delivered from capacitors that can be charged by taking current from the battery cells, each of which may also be part of the operational circuitry. The canister may be formed of titanium, stainless steel or other materials and may include coatings such as titanium nitride, iridium oxide, porous carbon, etc.

The leads may be formed of suitable biocompatible materials, and may be coated or uncoated. The leads may contain conductors made, for example, with stainless steel (including MP35N alloy), silver, etc., in various forms including single wires, braids, helically coiled wires and/or drawn filled tubes. The electrodes can be coated or uncoated and may also be formed of suitable materials such as MP35N, as well as any suitable stainless steel, platinum, gold, silver, titanium, or alloy thereof, for example.

In one embodiment, the present invention comprises a method of implanting a subcutaneous electrode, the elec-trode comprising an elongated shaft including a dielectric insulator and at least one electrical conductor therein, the elongated shaft having proximal and distal ends; at least a first electrode disposed near the distal end of the elongated shaft and coupled to at least one electrical conductor; a coupling assembly disposed near the proximal end of the elongated shaft configured to provide electric contact to the electrical conductor for connecting to an implantable medi-cal device; and a lead attachment structure disposed at the distal end of the elongated shaft, the lead attachment struc-ture including at least first and second flexible members disposed side-by-side and having means for attaching a suture. In this embodiment, the method comprises establish-ing a subcutaneous path using an insertion tool having a proximal end with a handle and a distal end configured for dissecting subcutaneous tissue and including an attachment feature; attaching a suture to the attachment feature and each of the means for attaching a suture on the flexible members; pulling the lead system into the subcutaneous path with the first and second flexible members disposed side-by-side; achieving a desired position lead system in the subcutaneous path; removing the suture from the means for attaching a suture; flexing the flexible members outward from their side-by-side disposition; and suturing the first and second flexible members to the subcutaneous tissue of the patient using the means for attaching a suture on each of the first and second flexible members.

In another embodiment, the present invention comprises another method of implanting a subcutaneous lead, the lead comprising: an elongated shaft including a dielectric insulator and at least one electrical conductor therein, the elongated shaft having proximal and distal ends; at least a first electrode disposed near the distal end of the elongated shaft and coupled to at least one electrical conductor; a coupling assembly disposed near the proximal end of the elongated shaft configured to provide electrical coupling to the electrical conductor for connecting to an implantable medical device; a distal attachment feature comprising first and second arms, each of the arms configured to allow a suture to be attached thereto, the arms being flexible such that the arms can be wrapped about a distal portion of the elongated shaft. In this embodiment, the method comprises, with the first and second arms wrapped about the distal end of the shaft, inserting the lead into the patient's subcutaneous tissue; unwrapping the first and second arms from about the distal end of the shaft; and suturing the first and second arms to the subcutaneous tissue.

In another embodiment, the present invention comprises another method of implanting a subcutaneous electrode, the subcutaneous lead having a proximal end with a connecting element thereon for connecting to an implantable pulse generator and a distal end having a lead fixation structure thereon, the method comprising making an incision at approximately the xiphoid of a patient (the xiphoid incision) to the left of the sternal midline; making an incision at a location located in the range of 8-18 cm superior to the xiphoid incision, 1-3 cm left of the sternum (the high incision), over the ribs of the patient and level with or inferior to the manubrium; inserting an insertion tool through the xiphoid incision and tunneling toward and out of the high incision, the insertion tool having a distal end adapted for subcutaneously dissecting and tunneling through tissue, the distal end of the insertion tool including an attachment feature; securing the proximal end of the lead to the distal end of the insertion tool by tying a suture and using the attachment feature; pulling the proximal end of the lead into the patient's subcutaneous tissue through the high incision and again out of the patient's subcutaneous tissue at the xiphoid incision; making an incision at approximately the left axilla of the patient, along the inframammary crease (the axillary incision); reinserting the insertion tool through the xiphoid incision and tunneling to the axillary incision until the attachment feature can be accessed by the axillary incision; cutting the suture; withdrawing the insertion tool via the xiphoid incision while holding the suture out of the axillary incision; pulling the proximal end of the lead into the subcutaneous tissue of the patient through the xiphoid incision and toward and through the axillary incision; connecting the connecting element of the subcutaneous lead to an implantable pulse generator; and inserting the implantable pulse generator into the subcutaneous tissue of the patient through the axillary incision.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable lead electrode for subcutaneous implantation in a patient and adapted for use in a cardiac stimulus or monitoring system, the lead electrode comprising: a distal region having at least one electrode and an anchoring structure; and a proximal region having a proximal end for coupling to an implantable cardiac stimulus device; wherein at least one electrical connector electrically couples the proximal end to the at least one electrode; characterized by the anchoring structure being relatively inflexible and sized such that it cannot be passed through subcutaneous tissue without extensive dissection so that, in order to implant the lead electrode, the proximal region must be pulled through tissue by securing an insertion tool to the proximal end and pulling the proximal end with the insertion tool without passing the distal region more than minimally into a tissue pocket.

2. The implantable lead electrode of claim 1 wherein the anchoring structure is generally in the form of a Y having first and second arms each including an attachment feature.

3. The implantable lead electrode of claim 1 wherein the anchoring structure is generally in the form of a Y having first and second arms each having no attachment features for suturing to tissue.

4. The implantable lead electrode of claim 1 wherein the proximal end includes a plug for attachment to an implantable cardiac stimulus device.

5. The implantable lead electrode of claim 4 further comprising a plug cap for placement over the plug during implantation of the implantable lead electrode, the plug cap including an attachment feature enabling attachment of the plug cap to a tool for implantation of the implantable lead electrode, the plug cap being removable once implantation is completed.

6. The implantable lead electrode of claim 4 further comprising a plug cap for placement over the plug during implantation of the implantable lead electrode, the plug cap including a suture hole allowing a suture to be attached to the plug cap to allow the proximal end of the lead electrode assembly to be pulled into a subcutaneous tissue tunnel during implantation of the implantable lead electrode, the plug cap being removable once implantation is completed.

7. The implantable lead electrode of claim 4 wherein the plug includes an attachment feature enabling attachment of the plug to a tool for implantation of the implantable lead electrode.

8. The implantable lead electrode of claim 4 wherein the plug includes a suture hole allowing a suture to be attached to the plug to allow the proximal end of the lead electrode assembly to be pulled into a subcutaneous tissue tunnel during implantation of the implantable lead electrode.

9. A method of implanting an implantable lead electrode in a subcutaneous location,
wherein the implantable lead electrode the lead electrode comprises:
a distal region having at least one electrode and an anchoring structure; and
a proximal region having a proximal end for coupling to an implantable cardiac stimulus device;

wherein at least one electrical connector electrically couples the proximal end to the at least one electrode;

characterized by the anchoring structure being relatively inflexible and sized such that it cannot be passed through subcutaneous tissue without extensive dissection so that, in order to implant the lead electrode, the proximal region must be pulled through tissue by securing an insertion tool to the proximal end and pulling the proximal end with the insertion tool without passing the distal region more than minimally into a tissue pocket;

the method comprising:
making an upper sternal incision on the chest of a patient;
making a xiphoid incision on the chest of the patient, the upper sternal incision being superior of the xiphoid incision;
making a lateral incision on the chest of the patient relatively near the patient's left axilla;
pulling the proximal end of the lead electrode through the upper sternal incision to the xiphoid incision;
pulling the proximal end of the lead electrode to the lateral incision; and coupling the proximal end of the lead electrode to an implantable medical device canister;
wherein the pulling steps are completed such that the anchoring structure is passed into the patient's tissue near the upper sternal incision to allow closing of the upper sternal incision, but without passage through of the anchoring structure through patient tissue toward the xiphoid incision.

10. The method of claim 9 wherein the anchoring structure of the lead electrode is generally in the form of a Y having first and second arms.

11. The method of claim 10 wherein the first and second arms each include an attachment feature, and the method further comprises attaching the attachment features to the subcutaneous tissue of the patient.

12. The method of claim 9 wherein the proximal end includes a plug for attachment to an implantable cardiac stimulus device and the method includes:
using an implantation tool to create one or more subcutaneous tunnels between the incisions; and
attaching the implantation tool to the plug for at least one of the pulling steps.

13. The method of claim 12 further comprising securing a suture between the implantation tool and the plug.

14. The method of claim 9 wherein the proximal end includes a plug for attachment to an implantable cardiac stimulus device and a plug cap for covering the plug during implantation, and the method includes:
using an implantation tool to create one or more subcutaneous tunnels between the incisions; and
attaching the implantation tool to the plug cap for at least one of the pulling steps.

15. The method of claim 14 further comprising securing a suture between the implantation tool and the plug cap.

16. The method of claim 9 further comprising applying a suture sleeve to the lead electrode near the xiphoid incision and securing the suture sleeve to the patient's subcutaneous tissue.

* * * * *